US010080748B2

(12) United States Patent
Heidenreich et al.

(10) Patent No.: US 10,080,748 B2
(45) Date of Patent: Sep. 25, 2018

(54) USE OF FLAP INHIBITORS TO REDUCE NEUROINFLAMMATION MEDIATED INJURY IN THE CENTRAL NERVOUS SYSTEM

(71) Applicants: Kim A. Heidenreich, Denver, CO (US); Robert C. Murphy, Denver, CO (US)

(72) Inventors: Kim A. Heidenreich, Denver, CO (US); Robert C. Murphy, Denver, CO (US)

(73) Assignee: Bioscience Pharma Partners, LLC, Phoenix, AZ (US)

( * ) Notice: Subject to any disclaimer, the term of this patent is extended or adjusted under 35 U.S.C. 154(b) by 0 days.

(21) Appl. No.: 14/613,658

(22) Filed: Feb. 4, 2015

(65) Prior Publication Data

US 2015/0216854 A1   Aug. 6, 2015

Related U.S. Application Data

(60) Provisional application No. 61/935,763, filed on Feb. 4, 2014.

(51) Int. Cl.
*A61K 31/4709* (2006.01)
*A61K 31/404* (2006.01)
(Continued)

(52) U.S. Cl.
CPC ........ *A61K 31/4709* (2013.01); *A61K 9/0043* (2013.01); *A61K 31/404* (2013.01); *A61K 31/405* (2013.01); *A61K 45/06* (2013.01)

(58) Field of Classification Search
None
See application file for complete search history.

(56) References Cited

U.S. PATENT DOCUMENTS

| 4,929,626 A | 5/1990 | Mohrs et al. |
| 4,970,215 A | 11/1990 | Mohrs et al. |

(Continued)

FOREIGN PATENT DOCUMENTS

| EP | 0623614 A1 | 11/1994 |
| WO | 9316069 | 8/1993 |

(Continued)

OTHER PUBLICATIONS

Voight et al.; "Effect of leukotriene inhibitors on evolution of experimental brain contusions"; 2012; Neuropathology and Applied Neurobiology; 38: 354-366; doi: 10.1111/j.1365-2990.2011.01211.x.*

(Continued)

*Primary Examiner* — Timothy P Thomas
(74) *Attorney, Agent, or Firm* — Dickinson Wright PLLC

(57) ABSTRACT

The present invention provides methods of attenuating or preventing brain injury mediated damage in the central nervous system by attenuating or preventing leukotriene-mediated events following a brain injury or long-term neuroinflammation after brain injury, in Alzheimer's disease, multiple sclerosis, stroke, and post-traumatic stress disorder. The methods comprise administering at least one 5-lipoxygenase activating protein (FLAP) inhibitor either before or after the brain injury. The method finds use in the treatment of traumatic brain injury (TBI), stroke, multiple sclerosis, Alzheimer's disease, post-traumatic stress disorder and other brain injuries associated with production of leukotrienes in the central nervous system. Preferably the FLAP inhibitor is administered intranasally and preferably for certain high risk individuals prophylactically prior to any potential brain injury event.

12 Claims, 29 Drawing Sheets

(51) Int. Cl.
*A61K 31/405* (2006.01)
*A61K 45/06* (2006.01)
*A61K 9/00* (2006.01)

(56) References Cited

U.S. PATENT DOCUMENTS

| | | |
|---|---|---|
| 5,081,138 A | 1/1992 | Gillard et al. |
| 5,095,031 A | 3/1992 | Brooks et al. |
| 5,126,354 A | 6/1992 | Mohrs et al. |
| 5,204,344 A | 4/1993 | Prasit et al. |
| 5,221,678 A | 6/1993 | Atkinson et al. |
| 5,229,516 A | 7/1993 | Musser et al. |
| 5,272,145 A | 12/1993 | Prasit et al. |
| 5,283,252 A | 2/1994 | Raddatz et al. |
| 5,288,743 A | 2/1994 | Brooks et al. |
| 5,292,769 A | 3/1994 | Mohrs et al. |
| 5,304,563 A | 4/1994 | Raddatz et al. |
| 5,399,699 A | 3/1995 | Kolasa et al. |
| 5,459,150 A | 10/1995 | Brooks et al. |
| 5,512,581 A | 4/1996 | Brooks et al. |
| 5,597,833 A | 1/1997 | Matzke et al. |
| 5,668,146 A | 9/1997 | Brooks et al. |
| 5,668,150 A | 9/1997 | Brooks et al. |
| 5,691,351 A | 11/1997 | Kolasa et al. |
| 5,714,488 A | 2/1998 | Brooks et al. |
| 5,783,586 A | 7/1998 | Kolasa et al. |
| 5,795,900 A | 8/1998 | Brooks et al. |
| 5,843,968 A | 12/1998 | Brooks et al. |
| 6,436,924 B2 | 8/2002 | Poppe et al. |
| 6,531,279 B1 | 3/2003 | Blumenfeld et al. |
| 6,545,019 B2 | 4/2003 | Posmantur et al. |
| 6,756,399 B2 | 6/2004 | Mulshine et al. |
| 7,405,302 B2 | 7/2008 | Hutchinson et al. |
| 7,795,274 B2 | 9/2010 | Hutchinson et al. |
| 7,834,037 B2 | 11/2010 | Hutchinson et al. |
| 7,951,831 B2 | 5/2011 | Hammock et al. |
| 7,977,359 B2 | 7/2011 | Hutchinson et al. |
| 8,158,362 B2 | 4/2012 | Helgadottir et al. |
| 8,399,666 B2 | 3/2013 | Hutchinson et al. |
| 8,546,431 B2 | 10/2013 | Hutchinson et al. |
| 8,598,359 B2 | 12/2013 | Sandanayaka et al. |
| 8,697,730 B2 | 4/2014 | Rewolinski et al. |
| 8,841,295 B2 | 9/2014 | Hutchinson et al. |
| 2001/0025040 A1 | 9/2001 | Poppe et al. |
| 2002/0022650 A1 | 2/2002 | Posmantur et al. |
| 2005/0113408 A1 | 5/2005 | Helgadottir et al. |
| 2007/0105866 A1 | 5/2007 | Hutchinson et al. |
| 2007/0123522 A1 | 5/2007 | Hutchinson et al. |
| 2007/0219206 A1 | 9/2007 | Hutchinson et al. |
| 2007/0225285 A1 | 9/2007 | Hutchinson et al. |
| 2007/0244128 A1 | 10/2007 | Hutchinson et al. |
| 2010/0068301 A1 | 3/2010 | Hutchinson et al. |
| 2010/0197687 A1 | 8/2010 | Pelcman et al. |
| 2013/0090315 A1 | 4/2013 | Vanlandingham et al. |
| 2013/0310421 A1 | 11/2013 | Pratico |

FOREIGN PATENT DOCUMENTS

| | | |
|---|---|---|
| WO | 9325546 | 12/1993 |
| WO | 0205825 A1 | 1/2002 |
| WO | 2007047207 A2 | 4/2007 |
| WO | 2007056021 A2 | 5/2007 |
| WO | 2007056220 A2 | 5/2007 |
| WO | 2009002746 A1 | 12/2008 |
| WO | 2010075314 A2 | 7/2010 |
| WO | 2010075315 A2 | 7/2010 |
| WO | 2011049979 A2 | 4/2011 |

OTHER PUBLICATIONS

Ilium; "Nasal drug delivery: new developments and strategies"; Drug Discovery Today; 2002; 7(23): 1184-1189.*

Chu et al.; "Involvement of 5-lipoxygenase activating protein in the amyloidotic phenotype of an Alzheimer's disease mouse model"; 2012; Journal of Neuroinflammation; 9:127; pp. 1-10.*

Heidenreich; NIH RePORTER; Project No. 1R21NS079435-01A1; start Date 2013.*

Metting et al.; "GFAP and S100B in the acute phase of mild traumatic brain injury"; Neurology. May 1, 2012;78(18):1428-33. doi: 10.1212/WNL.0b013e318253d5c7. Epub Apr. 18, 2012.*

Blyth et al.; "Elevated Serum Ubiquitin Carboxy-Terminal Hydrolase L1 is Associated with Abnormal Blood—Brain Barrier Function after Traumatic Brain Injury"; Journal of Neurotrauma 28:2453-2462 (Dec. 2011).*

International Search Report, Five (5) Pages, dated May 12, 2015.

C. Voigt et al., "Effect of Leukotriene Inhibitors on Evolution of Experimental Brain Contusions" Neuropathology and Applied Neurobiology, vol. 38, No. 4, May 11, 2012, pp. 354-366.

Hartig Wolfgang et al., "Impact of 5-Lipoxygenase Inhibitors on the Spatiotemporal Distribution of Inflammatory Cells and Neuronal Cox-2 Expression Following Experimental Traumatic Brain Injury in Rats", Brain Research, Elsevier, Amsterdam, NL, vol. 1498, Dec. 23, 2012, pp. 69-84.

Yoshikawa K et al., "Inhibition of 5-Lipoxygenase Activity in Mice During Cuprizone-Induced Demyelination Attenuates Neuroinflammation, Motor Dysfunction and Axonal Damage", Prostaglandins Leukotrienes and Essential Fatty Acids, Churchill Livingstone, Edinburgh, vol. 85, No. 1, Apr. 12, 2011, pp. 43-52.

Kai-Hsiang Kang et al., "Protection of Dopaminergic Neurons by 5-Lipoxygenase Inhibitor", Neuropharmacology, vol. 73, Oct. 1, 2013, pp. 380-387.

Santiago Farias et al., "Injury-Related Production of Cysteinyl Leukotrienes Contributes to Brain Damage Following Experimental Traumatic Brain Injury", Journal of Neurotrauma, vol. 26, No. 11, Nov. 1, 2009, pp. 1977-1986.

Hanson Leah R et al., "Intranasal Delivery Bypasses the Blood-Brain Barrier to Target Therapeutic Agents to the Central Nervous System and Treat Neurodegenerative Disease", BMC Neuroscience, Biomed Central, London, GB, vol. 9, No. Suppl 3, Dec. 10, 2008, p. S5.

Chelsea E. Corser-Jensen et al., "Blocking Leukotriene Synthesis Attenuates the Pathophysiology of Traumatic Brain Injury and Associated Cognitive Deficits", Experimental Neurology, vol. 256, Jun. 1, 2014, pp. 7-16.

Kiwak KJ, Moskowitz M, Levine L. Leukotriene production in gerbil brain after ischemic insult, subarachnoid hemorrhage, and concussive injury. J Neurosurg 1985; 62: 865-69 PMID: 3998837.

Westcott, JY, Murphy, RC, and Stenmark, K. Eicosanoids in human ventricular cerebrospinal fluid following severe brain injury. Prostaglandins 1987 34: 877-887.

Minamisawa H, Terashi A, Katayama Y, Kanda Y, Shimizu J, Shiratori T, Inamura K, Kaseki H, Yoshino Y. Brain eicosanoid levels in spontaneously hypertensive rats after ischemia with reperfusion: leukotriene C4 as a possible cause of cerebral edema. Stroke 1988; 19: 372-77 PMID: 3354024.

Dhillon H, Dose J, Prasad M. Regional generation of leukotriene C4 after experimental brain injury in anesthetized rats. J Neurotraum 1996; 13: 781-89 PMID: 9002063.

Hariri, R J, Ghajar, J B G, Pomeranz, K B, Hajjar, D P, Giannuzzi, R F, Tomich, E, Andrews, D W, Patterson, R H. Human glial cell production of lipoxygenase-generated eicosanoids: A potential role in the pathophysiology of vascular changes following traumatic brain injury. J Trauma 1989; 9: 1183-1307.

Ciceri P, Rabuffetti M, Monopoli A, Nicosia S. Production of leukotrienes in a model of focal cerebral ischemia in the rat. Brit J Pharmacol 2001; 133: 1323-29 PMID: 11498518.

Schuhmann MU, Mokhtarzadeh M, Stichtenoth DO, Skardelly M, Klinge PM, Gutzki FM, Samii M, Brinker T. Temporal profiles of cerebrospinal fluid leukotrienes, brain edema and inflammatory response following experimental brain injury. Neurol Res 2003; 25: 481-91 PMID: 12866196.

Zhang WP, Hu H, Zhang L, Ding W, Yao HT, Chen KD, Sheng WW, Chen Z, Wei EQ. Expression of cysteinyl leukotriene receptor 1 in human traumatic brain injury and brain tumors. Neurosci Lett 2004; 363: 247-51 PMID: 15182953.

(56) References Cited

OTHER PUBLICATIONS

Hu H, Chen G, Zhang JM, Zhang WP, Zhang L, Ge QF, Yao HT, Ding W, Chen Z, Wei EQ. Distribution of cysteinyl leukotriene receptor 2 in human traumatic brain injury and brain tumors. Acta Pharm Sinic 2005; 26: 685-90 PMID: 15916734.

Yu G, Wei E, Wang M, Zhang W, Zhang S, Weng J, et al. Pranlukast, a cysteinyl leukotriene receptor-1 antagonist, protects against chronic ischemic brain injury and inhibits the glial scar formation in mice. Brain Res 2005; 1053: 116-25 doi: 10.1016/j.plefa.2011.04.022. PMID: 21555210.

Chu LS, Wei EQ, Yu GL, Fang SH, Zhou Y, Wang ML, Zhang WP. Pranlukast reduces neutrophil but not macrophage/microglial accumulation in brain after focal cerebral ischemia in mice. Acta Pharmacol Sinic 2006; 27: 282-88 PMID: 16490162.

Fang SH, Wei EQ, Zhou Y, Wang ML, Zhang WP, Yu GL, Chu LS, Chen Z. Increased expression of cysteinyl leukotriene receptor-1 in the brain mediates neuronal damage and astrogliosis after focal cerebral ischemia in rats. Neuroscience 2006; 140: 969-79 PMID: 16650938.

Wang ML, Huang XJ, Fang SH, Yuan YM, Zhang WP, Lu YB, Ding Q, Wei EQ. Leukotriene D4 induces brain edema and enhances CysLT2 receptor-mediated aquaporin 4 expression. Biochem Bioph Res Co 2006; 350: 399-404 PMID: 17010308.

Qian XD, Wei EQ, Zhang L, Sheng WW, Wang ML, Zhang WP, Chen Z. Pranlukast, a cysteinyl leukotriene receptor 1 antagonist, protects mice against brain cold injury. Eur J Pharmacol 2006; 549: 35-40 PMID: 16973153.

Ding Q, Fang SH, Zhou Y, Zhang LH, Zhang WP, Chen Z, Wei EQ. Cysteinyl leukotriene receptor 1 partially mediates brain cryoinjury in mice. Acta Pharm Sinic 2007; 28: 945-52 PMID: 17588329.

Farias S, Frey LC, Murphy RC, Heidenreich KA. Injury-related production of cysteinyl leukotrienes contributes to brain damage following experimental traumatic brain injury. J Neurotrauma 2009; 26: 1977-86 doi: 10.1089/neu.2009.0877 PMID: 19886806.

Dhillon, HS, Donaldson, D, Dempsey, RJ, and Prasad M. Regional Levels of Free Fatty Acids and Evans Blue Extravasation After Experimekastntal Brain Injury. J Neurotrauma 2009; 11: 405-415.

Biber N, Toklu HZ, Solakoglu S, Gultomruk M, Hakan T, Berkman Z, Dulger FG. Cysteinyl-leukotriene receptor antagonist montelukast decreases blood-brain barrier permeability but does not prevent oedema formation in traumatic brain injury. Brain Injury 2009; 23: 577-84 doi: 10.1080/02699050902926317 PMID: 19484631.

Zhao, R, Shi, W, Zhang, Y, Fang, S, and Wei, E. Montelukast, a cysteinyl leukotriene receptor antagonist, attenuate chronic brain injury after focal cerebral ischemia in mice and rats. J. Pharmacy and Pharmacology 2011; 63: 550-557.

Voigt C, Donat CK, Hartig W, Förschler A, Skardelly M, Stichtenoth D, Arendt T, Meixensberger J, Schuhmann MU. Effect of leukotriene inhibitors on evolution of experimental brain contusions. Neuropath Appl Neuro 2012; 38: 354-66 doi: 10.1111/j.1365-2990.2011.01211.x. PMID: 218349 MK-886 or Boscari®, a mixture of boswellic acids.

Evans JF1, Lévillé C, Mancini JA, Prasit P, Thérien M, Zamboni R, Gauthier JY, Fortin R, Charleson P, MacIntyre DE, et al.; 5-Lipoxygenase-activating protein is the target of a quinoline class of leukotriene synthesis inhibitors; Mol Pharmacol. Jul. 1991;40(1):22-7.

Mancini JA1, Prasit P, Coppolino MG, Charleson P, Leger S, Evans JF, Gillard JW, Vickers PJ; 5-Lipoxygenase-activating protein is the target of a novel hybrid of two classes of leukotriene biosynthesis inhibitors; Mol Pharmacol. Feb. 1992;41(2):267-72.

Hatzelmann A1, Fruchtmann R, Mohrs KH, Raddatz S, Matzke M, Pleiss U, Keldenich J, Müller-Peddinghaus R.; Mode of action of the leukotriene synthesis (FLAP) inhibitor BAY X 1005: implications for biological regulation of 5-lipoxygenase; Agents Actions. Nov. 1994;43(1-2):64-8.

Ferguson AD1, McKeever BM, Xu S, Wisniewski D, Miller DK, Yamin TT, Spencer RH, Chu L, Ujjainwalla F, Cunningham BR, Evans JF, Becker JW; Crystal structure of inhibitor-bound human 5-lipoxygenase-activating protein; Science. Jul. 27, 2007;317(5837):510-2. Epub Jun. 28, 2007.

Muller-Peddinghaus, R. et al.; BAY X1005, a new inhibitor of leukotriene synthesis: In vivo inflammation pharmacology and pharmacokinetics; J. Pharmacol. Exp. Ther. 267, 51-57.

Gillard, J. et al.; L-663,536 (MK-886) (3-[1-(4-chlorobenzyl)-3-tbutyl-thio-5-isopropylindol-2-yl]-2,2-dimethylpropanoic acid), a novel, orally active leukotriene biosynthesis inhibitor; Can. J. Physiol. Pharmacol. 67, 456-464.

Miller, D.K. et al. (1990); Identification and isolation of a membrane protein necessary for leukotriene production; Nature 343, 278-28, Dixon, R.A.F. et al. (1990) Requirement of a 5-lipoxygenase-activating protein for leukotriene synthesis. Nature 343, 282-284).

Brideau, C. et al. (1992); Pharmacology of MK-0591 (3-[1-(4-chlorobenzyl)-3-(t-butylthio)-5-(quinolin-2-ylmethoxy)-indol-2-yl]-2,2-dimethylpropanoic acid), a potent, orally active leukotriene biosynthesis inhibitor; Can. J. Physiol. Pharmacol. 70, 799-807).

* cited by examiner

USE OF FLAP INHIBITORS TO REDUCE NEUROINFLAMMATION MEDIATED INJURY IN THE CENTRAL NERVOUS SYSTEM

RELATED APPLICATIONS

This application claims the benefit of U.S. Provisional Application No. 61/935,763 filed on Feb. 4, 2014.

STATEMENT REGARDING FEDERALLY SPONSORED RESEARCH

None.

TECHNICAL FIELD

This invention relates generally to a method of treating neuroinflammation and neuroinflammation mediated injury resulting from various brain injury events such as traumatic brain injury, stroke, multiple sclerosis, Alzheimer's disease, and post-traumatic stress disorder by administration of 5-lipoxygenase activating protein (FLAP) inhibitors.

BACKGROUND OF THE INVENTION

According to the Centers for Disease Control and Prevention (CDC), in the United States alone there are more than 2.5 million reported cases of traumatic brain injury (TBI) each year. It is believed that more than 5 to 6 million cases of TBI in the United States per year go unreported because they are not believed to be severe enough to be treated in hospital settings, designated as mild TBI (mTBI), and are thus treated in non-hospital settings or not treated at all. These statistics do not include the many TBI events, both mTBI and more severe TBI, suffered by our military personnel daily in the many conflicts that they are involved in outside the United States. These statistics also do not include the TBI events suffered by others outside the United States. It is only recently that the medical community has come to realize that the consequences of so called mild TBI may not be mild in the longer term. Epidemiological research has identified mTBI as a major public health concern. Clinical research evidence has emerged suggesting that for some patients even mTBI in addition to more severe TBI can lead to prolonged physical and neurocognitive symptoms months to years after the brain injury has occurred. The neuropathology of human TBI is characterized by diffuse axonal injury leading to alterations of functional connectivity of various brain regions and prolonged neuroinflammation as evidenced by reactive astrocytes, activated microglia, and microbleeds in gray matter regions and white matter tracts.

Acute and chronic brain injuries and degenerative disorders can activate resident brain cells such as astrocytes and microglia and recruit peripheral immune cells to injured brain regions resulting in amplified neuroinflammation and exacerbation of brain damage. Leukotrienes (LT) are potent bioactive lipids that mediate inflammation. Murphy R C, et a. *Proc Natl Acad Sci USA.* 76:4275-4279, 1979. Leukotriene biosynthesis is initiated by mechanical injury to cells and enzymatic cleavage of arachidonic acid (AA) from membrane glycerolphospholipids. Falco, G and Murphy R C, *Pharmacol, Rev.* 58, 375-388, 2006. The enzymatic action of 5-lipoxygenase (5-LO) and 5-lipoxygenase activating protein (FLAP) converts AA into leukotriene $A_4$ ($LTA_4$). The $LTA_4$ is quickly converted to leukotriene $B_4$ ($LTB_4$) by $LTA_4$-hydrolase or to leukotriene $C_4$ ($LTC_4$) by $LTC_4$-synthase. $LTC_4$ can then be converted to leukotriene $D_4$ ($LTD_4$) and leukotriene $E_4$ ($LTE_4$), and these three LTs ($LTC_4$, $LTD_4$, $LTE_4$) are collectively known as the cysteinyl leukotrienes. The actions of cysteinyl leukotrienes have been studied primarily in the context of asthma where they are known to induce vascular permeability, extravasation of large molecules, stimulation of cytokine release, and contraction of bronchial smooth muscle. Boyce J A, *Immunol. Rev.* 217, 168-185, 2007. Leukotrienes are undetectable in the healthy brain. Farias S, et al, *J. Neurotraum,* 26, 1977-1986, 2009. After traumatic brain injury (TBI) or stroke, however, leukotrienes are synthesized by a transcellular mechanism involving infiltrating neutrophils or endogenous microglia and endogenous brain cells. Farias S, *J. Neurochem.* 103, 1310-1318, 2007; Farias S, et al. *J. Neurotraum.* 26, 1977-1986, 2009.

It is desirable to provide a method to ameliorate the neuroinflammation and neurodegeneration that accompanies brain injury events such as TBI, stroke, multiple sclerosis, and Alzheimer's disease. In addition, some recent research seems to suggest that posttraumatic stress disorder (PTSD) may have a neurodegeneration component to it and thus it is also a potential candidate for a method to reduce neurodegeneration and neuroinflammation. It would be beneficial to prevent a range of the secondary physical effects and cognitive effects of these brain injury events.

SUMMARY OF THE INVENTION

The present invention demonstrates that the early production of leukotrienes after traumatic brain injury (TBI) signals adverse effects including blood brain barrier (BBB) disruption and edema, early detrimental events that lead to additional cell death, axonal injury, and neurologic impairments. In addition, the present invention discloses and shows that brain injury events lead to long term neuroinflammation in multiple brain regions. The present inventors have used two animal models of brain injury, specifically a rat fluid percussion injury model of TBI and a mouse closed head injury (CHI) model of mild TBI. The inventors believe that the results have implications for and suggest treatments for other brain injury events in addition to TBI including stroke, multiple sclerosis, Alzheimer's disease, and posttraumatic stress disorder (PTSD). The inventors have also discovered that blockade of leukotriene production by administration of FLAP inhibitors that reach the central nervous system (CNS) significantly blocks edema, BBB disruption, cell death, and neuroinflammation as well as cognitive and motor impairments that occur after TBI. FLAP inhibitors are known to have several feasible routes of peripheral administration including oral, intravenous, suppository, and intraperitoneal and have no reported toxicity or deleterious effects. The inventors provide evidence that an intranasal administration route, which bypasses the blood brain barrier, results in rapid delivery of FLAP inhibitors to the brain with relatively less drug delivered systemically into the blood and circulatory system. Thus, this class of anti-inflammatory agents provides promising new drug candidates for interventional therapy after TBI, stroke, multiple sclerosis, Alzheimer's disease, and post-traumatic stress disorder (PTSD). There is currently no treatment that mitigates brain damage and neurological dysfunction after TBI.

The present invention further discloses that when FLAP inhibitors are given prior to brain injury events, they mitigate cell death, edema, and cognitive deficits. Thus, in addition to using FLAP inhibitors shortly after brain injury to block or mitigate secondary injury or after prolonged neuroinflammatory settings, FLAP inhibitors have a potential prophylactic preventative role in brain injury events such as TBI, whereby individuals at high risk for head injury, including athletes in high contact sports and military personnel in combat scenarios, could be given FLAP inhibitors chronically or before an event that predisposes them to risk of head trauma or brain injury. Second generation FLAP inhibitors have longer half-lives and could therefore possibly be administered once daily for protection against brain injury. It is believed that the FLAP inhibitors of the present invention can also be used to treat neuroinflammation associated with stroke, multiple sclerosis, Alzheimer's disease, and post-traumatic stress disorder.

A drug that blocks or attenuates secondary brain damage after TBI would likely prevent the majority of deaths and long-term disabilities after TBI. Nasal delivery of drugs has several major advantages over other drug delivery methods: 1) nasal drug delivery bypasses the BBB thereby increasing brain bioavailability and allowing for use of compounds that cannot pass through the blood brain barrier, 2) nasal drug delivery limits the amount of drug entering the systemic circulation thus decreasing the potential for liver and heart toxicity. 3) nasal delivery of drugs is very rapid, a factor critical for TBI intervention, and 4) the method of nasal delivery is quick and simple making it very suitable to a prophylactic use setting or to delivery of treatment shortly after the TBI event.

In one embodiment the present invention is a method of treating neuroinflammation caused by a brain injury event in an animal comprising the steps of providing a 5-lipoxygenase activating protein (FLAP) inhibitor, wherein the FLAP inhibitor is able to cross the blood brain barrier of an animal; administering the FLAP inhibitor to the animal in an amount and at a time either before a brain injury event or a time after a brain injury event wherein the amount and the time is sufficient for the FLAP inhibitor to reduce a level of leukotrienes produced in a brain of the animal as a result of the brain injury event.

In one embodiment the present invention is a method of reducing central nervous system neuroinflammation mediated damage resulting from a brain injury event in an animal comprising the steps of providing a 5-lipoxygenase activating protein (FLAP) inhibitor, wherein the FLAP inhibitor is able to cross the blood brain barrier of an animal; administering the FLAP inhibitor to an animal in an amount and at a time either before a brain injury event or a time after a brain injury event wherein the amount and the time is sufficient for the FLAP inhibitor to reduce the central nervous system neuroinflammation mediated damage as a result of the brain injury event in the animal.

In one embodiment the present invention is method of treating neuroinflammation caused by a brain injury event in an animal comprising the steps of: providing a 5-lipoxygenase activating protein (FLAP) inhibitor; administering the FLAP inhibitor to the animal via an intranasal route in an amount and at a time either before a brain injury event or a time after a brain injury event wherein the amount and the time is sufficient for the FLAP inhibitor to reduce a level of leukotrienes produced in a brain of the animal as a result of the brain injury event.

In one embodiment the present invention is a method of reducing central nervous system neuroinflammation mediated damage resulting from a brain injury event in an animal comprising the steps of providing a 5-lipoxygenase activating protein (FLAP) inhibitor; administering the FLAP inhibitor to an animal via an intranasal route in an amount and at a time either before a brain injury event or a time after a brain injury event wherein the amount and the time is sufficient for the FLAP inhibitor to reduce the central nervous system neuroinflammation mediated damage as a result of the brain injury event in the animal.

These and other features and advantages of this invention will become more apparent to those skilled in the art from the detailed description of a preferred embodiment. The drawings that accompany the detailed description are described below.

BRIEF DESCRIPTION OF THE DRAWINGS

FIG. 8A is a representative fluorescence image of EB (red) uptake by hippocampal cell layers and DAPI uptake (blue) in the ipsilateral hippocampus 5 hours after TBI, FIG. 8B is a higher magnification of images of EB extravasation in the ipsilateral CA1 hippocampal cell layer in animals that received either vehicle or MK-886 15 minutes after TBI, and FIG. 8C is a graph showing quantitation of EB+ cells, EB-DAPI colocalization, in the hippocampal regions, Bar=200 µm;

DETAILED DESCRIPTION OF A PREFERRED EMBODIMENT

Figure 1:
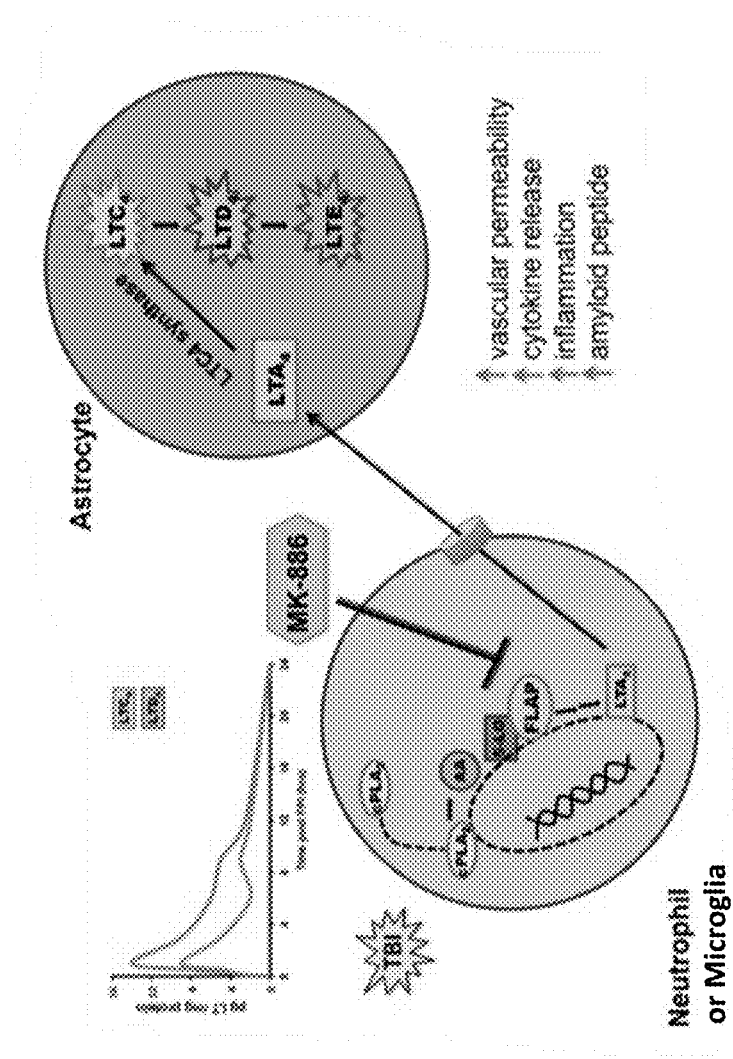
FIG. 1 is a schematic demonstrating transcellular biosynthesis of leukotrienes in brain tissue immediately following, and in response to a brain injury event or neuroinflammation.

The following abbreviations and terms are used throughout the specification and claims and have the defined meanings unless noted otherwise: arachidonic acid (AA); 5-lipoxygenase (5-LO); blood-brain barrier (BBB); Evan's Blue (EB); field excitatory post-synaptic potential (fEPSP); 5-lipoxygenase activating protein (FLAP); fluid percussion injury (FPI); long-term potentiation (LTP); radial arms water maze (RAWM); reverse-phase liquid chromatography coupled to tandem mass spectrometry (RP LC-MS/MS); traumatic brain injury (TBI); human whole blood (HWB);

the term animal is a general term meant to include all members of the animal kingdom, including all mammals, such as, humans, domesticated animals and undomesticated animals; closed head injury (CHI) especially in reference to the mouse model described in the present specification; Hematoxylin and Eosin (H&E); glial fibrillary acidic protein (GFAP); ubiquitin carboxy-terminal hydrolase L-1 (UCHL-1), myeloperoxidase (MPO), ionized calcium-binding adapter molecule 1 (Iba-1), milligram (mg), milliliter (ml or mL), picogram (pg), nanogram (ng), millimeter (mm), days post injury (dpi).

The protein 5-lipoxygenase activating protein was discovered in the late 1980s and early 1990s in screens for leukotriene inhibitors. The enzymatic action of 5-lipoxygenase (5-LO) and 5-lipoxygenase activating protein (FLAP) converts arachidonic acid (AA) from membrane glycerolphospholipids into leukotriene $A_4$ ($LTA_4$). This initiates the leukotriene cascade wherein $LTA_4$ is quickly converted to leukotriene $B_4$ ($LTB_4$) by $LTA_4$-hydrolase or to leukotriene $C_4$ ($LTC_4$) by $LTC_4$-synthase. The $LTC_4$ can then be converted to leukotriene $D_4$ ($LTD_4$) and leukotriene $E_4$ ($LTE_4$), and these three leukotrienes ($LTC_4$, $LTD_4$, $LTE_4$) are collectively known as the cysteinyl-leukotrienes.

Shortly after the discovery of FLAP, inhibitors of FLAP including the indole MK-886, the quinoline BAY X1005, and the quinoline-indole MK-591 were developed and tested in human trials of asthma. B. S. Friedman, E. H. Bel, A. Buntiux, W. Tanaka, Y. H. Han, S, Shingo, R. Spector, P. Stork, Oral leukotriene inhibitor (MK-886) blocks allergen-induced airway responses. *Am. Rev. Respir. Dis.* 147, 839-844 (1993); B. Dahlén, M. Kumlin, E. Ihre, O. Zetterström, S. E. Dahlén, Inhibition of allergen-induced airway obstruction and leukotriene generation in atopic asthmatic subjects by the leukotriene biosynthesis inhibitor BAYx 1005. *Thorax* 52, 342-347 (1997); Z. Diamant, M. C. Timmers, H. Van Der Veen, B. S. Friedman, M. De Smct, Depre, L. Hilliard, E. H. Bel, P. J. Sterk, The effect of MK-0591, a novel 5-lipoxygenase activating protein inhibitor, on leukotriene biosynthesis and allergen-induced airway responses in asthmatic subjects in vivo. *J. Allergy clin. Immun.* 95, 42-51 (1995). All of these initially developed FLAP inhibitors demonstrated good safety profiles and efficacy in blocking leukotriene production in asthma patients, but were discontinued when the leukotriene receptor antagonists zafirlukast (Accolate™), montelukast (Singulair™) and pranlukast (Onon™) and the 5-LO inhibitor zileuton (Zyflo™) were brought to market and approved for treating asthma. The FLAP inhibitor MK-886 is 1-[(4-Chlorophenyl)methyl]-3-[(1,1-dimethylethyl)thio]-α,α-dimethyl-5-(1-methylethyl)-1H-Indole-2-propanoic acid. The FLAP inhibitor MK-591 is (3-[1-(4-chlorobenzyl)-3-(t-butylthio)-5-(quinolin-2-yl-methoxy)-indol-2-yl]-2,2-dimethyl propanoic acid. The FLAP inhibitor BAY-X1005 is (R)-α-Cyclopentyl-4-(2-quinolinylmethoxy)benzerteacetic acid.

Since the discovery of the FLAP inhibitors listed above others have been developed and this continues to be an area of further drug development. All FLAP inhibitors may find use in the present invention depending on the route of administration according to the present invention and those specifically mentioned are merely examples of suitable compounds and are not the only useful FLAP inhibitors. In one embodiment of the present invention, the FLAP inhibitor is administered systemically via one of the following routes: an intravenous injection, an intraperitoneal route, an oral route, or as a suppository. When administered by any of these routes a suitable FLAP inhibitor is one that is capable of crossing the blood brain barrier to a sufficient extent to provide enough bioavailable FLAP inhibitor to the brain regions to inhibit FLAP sufficiently to lead to a reduction in brain leukotriene related neuroinflammation. The partition coefficient, as known to one of skill in the pharmaceutical art, of the selected FLAP inhibitor preferably is sufficient to allow for concentration in the central nervous system and more specifically in the brain relative to concentration in the circulatory system and other tissues. Preferably the FLAP inhibitor has a half maximal inhibitory concentration (IC50) toward FLAP of 10 nanomolar or less, more preferably 5 nanomolar or less.

In another embodiment of the present invention the FLAP inhibitor is administered via an intranasal route. When a FLAP inhibitor is administered via this route the FLAP inhibitor is able to bypass the blood brain barrier and enter the brain directly via the nasal mucosa and by traveling along the trigeminal and olfactory neural pathways through extracellular mechanisms to gain entry to the brain. For this route the ability of the FLAP inhibitor to cross the blood brain barrier is not necessary as the route avoids the blood brain barrier. The FLAP inhibitor is prepared in a carrier that can comprise a lipid, one or more vegetable oils, phosphatidylserine, or mixtures thereof. This route permits use of nonpolar FLAP inhibitors since the blood brain barrier is avoided.

Other examples of FLAP inhibitors useful in the present invention besides MK-591 and MK-886 include, for example: 3-[3-tert-butylsulfanyl-1-[4-(6-ethoxypyridin-3-yl)benzyl]-5-(5-methylpyridin-2-ylmethoxy)-1H-indol-2-yl]-2,2-dimethylpropionic acid 11 cc (formerly AM803 now GSK-2190915 of GlaxoSmithKline); and 1-pentyl-3-(2-iodobenzoyl)indole (AM679 a cannabinoid).

The present invention is directed toward use of FLAP inhibitors to ameliorate the secondary neuroinflaminatory mediated neurodegeneration associated with brain injury events. Some of the brain injury events that are believed to be ameliorated by use of FLAP inhibitors include, by way of example, traumatic brain injury (TBI), post-traumatic stress disorder (PTSD), stroke, multiple sclerosis, Parkinsonism, and Alzheimer's disease.

FIG. 1 is a schematic demonstrating transcellular biosynthesis of leukotrienes in brain tissue in immediate response to a brain injury event, such as a TBI. Damaged cells and axons from the primary injury leak adenosine triphosphate (ATP) and glutamate that bind to microglial receptors and thereby induce calcium influx. The calcium influx activates the calcium-dependent cytosolic phospholipase A2 ($cPLA_2$). This phospholipase liberates AA from membrane phospholipids and the AA is converted to 5-hydroxyeicosatetraenoic acid (5-HETE) and then to $LTA_4$ by the dual action of 5-LO and its activating protein, FLAP. The produced $LTA_4$ is then converted by $LTA_4$ hydrolase to $LTB_4$, a potent chemotactic mediator that recruits neutrophils, or it is transported out of microglia and taken up by neighboring astrocytes and possibly neurons and converted to $LTC_4$, $LTD_4$, and $LTE_4$ through the action of $LTC_4$-synthase. The early production of leukotrienes promotes inflammation, BBB disruption, and edema that in turn lead to additional cell death, axonal injury, and neurologic impairments. As will be shown in the present specification, blockade of leukotriene production by FLAP inhibitors like MK-886 significantly blocks edema, cell death, and neurological impairments. As shown further in FIG. 1, the time course of production of $LTC_4$, upper trace, and $LTD_4$, lower trace, shown in the insert graph, shows a peak within the 4 hours following a TBI and then falls to zero by 24 hours post-TBI.

In the present specification, as will be described more fully below, we present two models of TBI in two species, rat and mouse. In the rat model the TBI event is induced using a lateral fluid percussion injury (FPI) while in the mouse model a TBI event is induced using a closed head injury (CHI) through use of an electromagnetically controlled piston device, ImpactOne. Both models show the value of the present invention in ameliorating the effects of a TBI.

EXPERIMENTAL PROTOCOLS

Animals

Adult male Sprague Dawley rats (9-11 weeks old, 250-300 g; Harlan Laboratories) were housed individually in temperature- and light-controlled housing with free access to food and water ad libitum, Adult male C57 B16/J mice (10-12 weeks old) were housed individually in temperature and light controlled housing with free access to food and water ad libitum. All procedures as described were performed under protocols approved by the University of Colorado Institutional Animal Care and Use Committee and in compliance with National Institutes of Health (NIH) Guide for the Care and Use of Laboratory Animals.
Experimental Traumatic Brain Injury (TBI) Model: Rat Lateral Fluid Percussion Injury (FPI)

Craniotomy and lateral fluid percussion injury (FPI) were performed using a previously validated and published procedure. Farias S, et al. *J. Neurotraum*, 26, 1977-1986, 2009; Frey L. C. et al. *J. Neurosci. Methods* 177, 267-272, 2009. Throughout the specification animals subjected to this protocol are referred to as having a TBI since this treatment protocol is a TBI model. Briefly, rats were anesthetized with 3-5% isoflurane, isosol, VEDCO Inc., St. Joseph, Mo., via nose cone and mounted in a stereotaxic head frame. A 3 millimeter (mm) craniotomy was created and centered at 3 mm caudal to bregma and 3.5 mm left of the sagittal suture, keeping the exposed dura intact. One steel support screw was embedded in the skull on the contralateral side. A Luer-Lock hub with an inside diameter of 3.5 mm was centered over the craniotomy and bonded to the skull with cyanoacrylate adhesive and capped. Dental acrylic, Snap, Parka, Inc., Edgewood, N.J., was poured around the huh and screw. After the acrylic hardened antibiotic ointment was applied around the cap and the animals were returned to their cages. The next day, approximately 15-20 hours later, animals were anesthetized with isoflurane in an induction chamber, immediately connected to the FPI apparatus, and received a 20 millisecond (ms) pulse of pressurized sterile saline at 2.7 atmospheres (atm) of pressure to simulate a moderate severity impact on the intact dural surface through the craniotomy before awakening from anesthesia. Sham-injured animals underwent craniotomy and were anesthetized and connected to the FPI apparatus, but they did not receive the fluid pulse. All animals received a subcutaneous injection of the analgesic, buprenorphine, 0.05 milligram/kilogram (mg/kg) Buprenex, prior to craniotomy, and subsequent injections every 12 hours for two days. Moistened food pellets were provided after injury, and all animals were monitored daily for well-being and weight changes.
Experimental Traumatic Brain Injury (TBI) Model: Mouse Closed Injury (CHI)

Briefly, the adult male mice were anesthetized with 3-5% isoflurane via a nose cone. The skull was exposed by a midline scalp incision. Mice were then mounted into a stereotaxic frame and an impact was delivered to the left parietal cortex using an electromagnetically controlled piston device ImpactOne. The angle was set at 20°, probe size was 5 mm, velocity was 5 meters/second, dwell time was 100 milliseconds. Sham-injured mice underwent the same procedures through stereotaxic mounting, however no impact was delivered. All animals received a subcutaneous injection of the analgesic, buprenorphine, 0.05 milligram/kilogram (mg/kg) Buprenex, prior to the scalp incision, and subsequent injections every 12 hours for two days. Moistened food pellets were provided after injury, and all animals were monitored daily for well-being and weight changes.

Vinblastine Administration

Two groups of four rats each were subjected to FPI as described above. Four days prior to the FPI, each animal was briefly anesthetized for less than 5 minutes with 3-3.5% isoflurane and administered either NaCl 0.9%, 2 ml/kg IV (vehicle) or vinblastine sulfate 0.5 mg/kg IV in an identical volume. Neutrophil depletion was verified by complete cell blood counts (CBC) in vinblastine treated animals 4 days after administration. Both groups were euthanized by decapitation and the brain lipids extracted 1 hour after FPI. The amounts of $LTC_4$ formed, measured by RP LC-MS/MS and normalized per milligram of protein, were compared between groups using one-way analysis of variance and the Student-Newman-Keuls test for multiple comparisons.

Intravenous Administration of FLAP Inhibitor MK-886 and Vehicle

The indole FLAP inhibitor MK-886 was prepared at a dose of 2.5 milligram/milliliter (mg/ml), dissolved in dimethyl sulfoxide (DMSO) and then diluted with 0.9% saline to 10% DMSO. The rats were briefly anesthetized with 3-3.5% isoflurane and either MK-885 at a dose of 6 mg/kg or vehicle was administered intravenously (IV) by tail vein injection. All animals were allowed to wake before undergoing additional procedures.

Measurement of Leukotrienes in Rodent Brain

Extraction of Rat Brain Lipids.
Cortical and hippocampal regions from ipsilateral and contralateral hemispheres were collected in 4 ml of 80% methanol, homogenized with a Dounee homogenizer, and internal standards were added to the homogenates. Protein content was measured using bicinchoninic acid assay (BCA) for protein to normalize lipid levels to the amount of tissue. Samples were centrifuged and the supernatant was collected. Samples were diluted to a final methanol concentration of lower than 15% and then the lipids were extracted using a solid phase extraction cartridge, Strata C18-E, 100 mg/1 ml, Phenomenex, Torrence Calif. The eluate, 1 ml of methanol, was dried down and reconstituted in 70 microliters (μl) of High Performance Liquid Chromotography (HPLC) solvent A, which is 8.3 mM acetic acid buffered to pH 5.7 with $NH_4OH$, plus 20 ml of solvent B, which is acetonitrile/methanol, 65/35, v/v.
Reverse-Phase Liquid Chromotography Coupled to Tandem Mass Spectrometry (RP LC-MS/MS) Measurement of Leukotrienes.
An aliquot of each sample, 35 μl, was injected into an HPLC system and subjected to reverse-phase chromatography using a C18 column (Columbus 150×1 mm, 5 μm Phenornenex) and eluted at a flow rate of 50 μl/minute with a linear gradient from 25% to 100% of mobile phase solvent B Solvent B was increased from 25% to 85% by 24 minutes, to 100% by 26 minutes, and held at 100% for a further 12 minutes. The HPLC effluent was directly connected to the electrospray source of a triple quadrupole mass spectrometer (Sciex API 2000, PE-Sciex, Thornhill, Ontario, Canada) and mass spectrometric analyses were performed in the negative ion mode using multiple reaction monitoring (MRM) of the specific transitions, m/z 624→272 for $LTC_4$, m/z 495→177 for $LTD_4$, m/z 335→195 for $LTB_4$, m/z 339→197 for d4-$LTB_4$, and m/z 629→277 for d5-$LTC_4$. Quantitation was performed using a standard isotope dilution curve as previously described, Farias et al., *J. Neurochem*, 103, 1310-1318, 2007, with reference leukotriene standards and stable isotope analogs from Cayman Chemical, Ann Arbor, Mich.

Magnetic Resonance Imagining (MRI)

Acquisition.

All MRI studies were performed in the University of Colorado Animal Imaging Shared Resource (AISR) facility Rats from the FPI model underwent MRI imaging at 72 hours after injury, using T2-weighted and Gd-enhanced T1-weighted sequences. Mice underwent MRI imaging at 7 and 30 dpi, using T2-weighted sequences. For all MRIs, the ranimals were anesthetized with 2.5% isoflurane. Scans were done using a 4.7 Tesla Bremner PharmaScan, and a quadrature birdcage coil with an inner diameter of 38 mm, tuned to the $^1H$ frequency of 200.27 MHz, was used for RF transmission and reception. T2-weighted axial MR scans were acquired using a RARE (rapid acquisition with relaxation enhancement) sequence with the following parameters: FOV: 4.6 cm; TE/TR: 32/5000 msec; slice thickness=1.20 mm; interslice distance 1.20 mm (no gap); number of slice=20; number of averages=4 per phase encode step; matrix size=128×256. T1-weighted MR images were acquired using a MSME (multi-slide multi-echo) sequence, both before and after administration of 0.2 mmol/kg Multiharice® IV (TE/TR of 11.0/700 msec).

T2-Weighted MRI Analysis.

For each rat, five slices, 1.2 mm thick, spanning the entire area of injury were used to calculate FPI-related brain swelling. The diameter of the injured, ipsilateral hemisphere was measured from midline to the widest point of the cortex (Fiji/ImageJ, NIH). The difference between the ipsilateral (ipsi) and contralateral (contra) hemisphere diameters was then calculated and normalized to the diameter of the contralateral hemisphere using the formula:

{(diameter Ipsi−diameter Contra)/diameter Contra}×100

T1-Weighted MRI Analysis.

For each rat, all images that exhibited a visible difference between ipsilateral and contralateral T1-weighted post-Gd hyperintensity in the leptomeninges were analyzed. There was no detectable leptomeningeal hyperintensity in the pre-Gd images. Fiji (ImageJ) software was used to outline and calculate the area of pixel intensity in each slice, which was then multiplied by 1.2 mm, the distance between successive MR images, to obtain a volume T1-weighted post-Gd hyperintensity. Volumes from all selected slices from each rat were summed to obtain a total volume of leptomeningeal Gd extravasation for each rat. The average value among all rats within a group is reported in $mm^3$.

General Procedure for Brain Fixation Prior to Histochemical Staining

At the indicated time points animals were deeply anesthetized with sodium pentobarbital, 50 mg/kg IP and transcadially perfused with ice-cold heparinized saline followed by freshly prepared 4% paraformaldehyde in Phosphate Buffered Saline (PBS). Brains were removed and post-fixed in 4% paraformaldehyde/PBS for four hours at 4° C. Brains were then cryoproteeted in 20% sucrose in PBS at 4° C., embedded in O.C.T. compound from Sakura Finetek USA Inc., Torrance, Calif. and stored at −70° C. until sectioned.

Evans Blue Administration and Extravgatianuly

One hour prior to FPI, rats received a 5 ml intraperitoneal (IP) injection of Evans Blue (EB) solution, 2% w/v in saline. Six hours post-FPI, rats were deeply anesthetized with sodium pentobarbital, 50 mg/kg IP, and transcardially perfused with 200 ml ice-cold heparinized saline, followed by 100 ml freshly prepared 4% paraformaldehyde in Phosphate Buffered Saline (PBS). Brains were removed and post-fixed in 4% paraformaldehyde/PBS for four hours at 4° C., Brains were then cryoprotected in 20% sucrose in PBS at 4° C., embedded in O.C.T. compound from Sakura Finetek USA Inc., Torrance, Calif. and stored at −70° C. Whole brains were sectioned coronally at 30 μm, and representative slices spanning the entire hippocampus at 270 μm increments from each animal were mounted onto slides and cover-slipped with Fluoromount-G containing 4',6-diamidino-2-phenylindole (DAPI) SouthernBiotech, Birmingham, Ala. Images of EB-positive brain regions were captured using a Zeiss Axioplan2 microscope equipped with a HB0100w/2 lamp, a Photornetics CoolSnapfx camera Roper Scientific, and IPLab software BD Biosciences. Images from each slice were stitched together using Fiji/ImageJ (NIH), and EB-positive cells in the hippocampal cell layers were quantified using the cell counter tool.

Electrophysiology

Hippocampal Slice Preparation.

Four days after FPI or at the times indicated in the figures for CHI model animals were sacrificed and the brains were rapidly removed and immersed in ice-cold, sucrose containing cutting buffer (87 mM NaCl, 2.5 mM KCl, 7 mM $MgCl_2$, 0.5 mM $CaCl_2$, 1.25 mM $NaH_2PO_4$, 25 mM D-glucose, 35 mM sucrose, and 25 mM NaHCO3) for 40-60 seconds to cool the interior of the brain. Transverse slices 400 μm an in thickness were made using a McIlwain Tissue Chopper and the slices were stored individually for recovery, at least 60 min. After recovery, a single slice was transferred to a recording chamber and superfused with artificial cerebrospinal fluid (aCSF) at a bulk flow rate of 2-3 ml/min at 31° C. The aCSF contained the following: 126 mM NaCl, 3.0 mM KCl, 1.0 mM $MgSO_4$, 2.0 mM $CaCl_2$, 1.2 mM $NaH_2PO^4$, 11 mM D-glucose, and 25.9 mM NaHCO3. A bipolar tungsten stimulating electrode was placed in the Schaffer collateral (SC) pathway to evoke synaptic field excitatory postsynaptic potentials (fEPSPs) recorded in the stratum radiatum using a nearby glass micropipette filled with aCSF.

Baseline Recordings.

Before each experimental run on a slice, an input-output curve was generated by increasing the stimulus voltage and recording the synaptic response until either a maximum was reached, or evidence of a population spike was observed on the fEPSP response. Also, a paired-pulse ratio (PPR) was run whereby pairs of stimuli were delivered to CA3 axons at an intrastimulus interval of 50 ms, PPR was quantitated as the {(amplitude of the second fEPSP)/(amplitude of the first fEPSP)}×100.

Measurement of Long-Term Potentiation.

The fEPSP responses were evoked with bipolar tungsten electrodes placed in the CA3 to CA1 dendritic field layer. Test stimuli were delivered once every 20 seconds with the stimulus intensity set to 40-50% of the maximum synaptic response. High-frequency stimulation (HFS) consisted of two trains of 100 Hz stimuli lasting 1 second each, with an inter-train interval of 20 seconds, at the control stimulus intensity. The fEPSP recordings were made with a glass micropipette filled with artificial cerebrospinal fluid (aCSF) and placed in the stratum radiatum approximately 200-300 µm from the cell body layer. This stimulation produced a long-term potentiated response (LTP) that persisted for more than 60 minutes in control or sham operated animals. The slopes of fEPSPs were calculated as the slope measured between 10-30% from the origin of the initial negative deflection. Each time point shown is an average of at least six 20-second interval measurements.

Radial Arms Water Maze Testing of Rats

The radial arms water maze (RAWM) consists of six 50 centimeter (cm) radial arms emanating from a circular area in a 160 cm diameter tank of 20.5° C. water, surrounded by 4 walls, each with a unique pattern. An escape platform was situated at the end of one of the arms and submerged below the surface of black opaque water, non-toxic Dust Free Black Powder Paint, Rich Art. Rats were handled, 2 minutes each, the day before craniotomy and three days after FPI. Training on Day 1 and 4 days post-FPI consisted of placing the animal in one of the aims and giving the animal a maximum of 60 seconds to find the platform in the goal arm. If the animal did not find the escape platform within 60 seconds, it was guided to the goal arm and allowed to stay on the platform for 15 seconds. Fifteen trials were administered with a five-minute inter-trial interval. The start arm for each trial was determined in a pseudorandom fashion with three randomized sequences of the live non-goal arms. The start and goal arms were different for each rat, but equivocal relative to goal arm location, to avoid position and place preferences. Testing, Day 2, the following day consisted of 15 swim trials. The platform remained in the Day 1 goal arm for the first five trials and was then moved to a new arm for trials 6-15. The start arm for each trial was determined in a pseudorandom fashion so the animal did not start in the Day 1 goal arm until after all other arms (trial 10). Videos for each of the 30 trials per animal were analyzed using Topscan (Cleversys Inc.) tracking software for errors and perseverance duration. Errors are defined as entry into a non-goal arm or entry into goal arm without reaching the platform.

Intranasal Administration of FLAP Inhibitor MK-591

For intranasal delivery and subsequent tissue collection, rats were anesthetized with 3.5% isoflurane and placed in a supine position on top of a heating pad. The quinoline-indole FLAP inhibitor MK-591, 60 micrograms (µg) formulated with a lipid carrier was administered using a P20 pipette. Specifically, 4 µl drops were formed at the pipette tip and lowered to alternating nostrils every two minutes until a total of eight 4 µl drops were administered. At 30 minutes after the start of intranasal delivery, blood was collected from the heart, and rats were transcardially perfused with 60 ml ice-cold 0.9% NaCl followed by 360 ml 4% paraformaldehyde at 15 ml/minute. Brain tissues were dissected into anatomical regions on ice, weighed, snap-frozen in liquid $N_2$, and stored at −70° C. until analysis. The levels of MK-591 in tissues and plasma were measured by tandem mass spectroscopy.

Mouse Histochemistry and Immunohistochetnistry

The mice, sham and CHI treated, were treated as described above in the general brain fixation procedure to prepared the paraffin embedded brains. For histochemical staining of H&E, and for immunohistochemical staining of myeloperoxidase (MPO), glial fibrillary acidic protein (GFAP), and ionized calcium-binding adapter molecule 1 (Iba-1) the sections were 6 microns thick. The stained slides were scanned, uploaded and viewed using Aperio ImageScope software. The staining was quantified using the Aperio software and its Positive Pixel Count Algorithm of Image Scope which compares the fraction of strong positive pixels to total stained pixel for a designated image region.

Statistical Analyses

All data shown are mean+/−standard error of the mean unless otherwise noted. Results were analyzed in SPSS 20 (IBM) or Prism 5.0 (GraphPad). All analysis used two-tailed non-paired student's t-tests for two groups, and one-way ANOVA for two or more groups followed by Tukey's HSD for multiple comparisons unless otherwise noted. The LTP I-O curves were analyzed with a two-way repeated measures ANOVA. The RAWM day one learning curves were collapsed into groups of three swims and analyzed with a two-way repeated measures ANOVA followed by a one-way ANOVA of each collapsed time point. The RAWM perseverance between trials one and three of the reversal task was expressed as a percentage of starting value (swim one=100%; swim threeo=swim three/swim onex100) and analyzed with a within subjects two-way repeated measures ANOVA, followed by a two-tailed student's paired t-test between the two trials. Alpha was set as $p<0.05$ to determine, significance in all tests.

Experimental Results Rat FPI Model

Figures 2A, 2B:
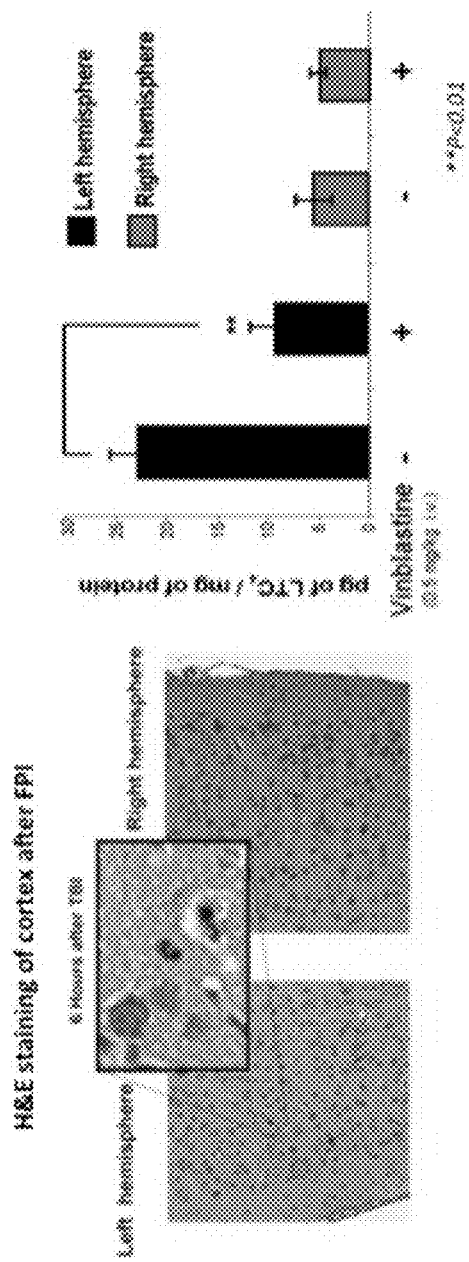
FIG. 2A, left panel, shows Hematoxylin and Eosin (H&E) staining of the cortex 6 hours after a TBI for both the ipsalateral left hemisphere and the contralateral right hemisphere.
FIG. 2B, right panel, demonstrates that neutrophils or monocytes contribute to injury induced leukotriene production in the brain after TBI as evidenced by the effects of pre-treatment with vinblastine.

FIG. 2A, left panel, shows Hematoxylin and Eosin (H&E) staining of the cortex 6 hours after a TBI for both the ipsalateral left hemisphere and the contralateral right hemisphere in rats subjected to the FPI model. The H&E staining 6 hours post-TBI shows that in the ipsalateral hemisphere there is evidence of extensive cell damage, while the contralateral hemisphere shows more intact cells and far less damage. FIG. 2B, right panel, demonstrates that neutrophils contribute to injury induced leukotriene production in the brain after TBI as evidenced by the effects of vinblastine. In the rat model, after TBI the levels of $LTC_4$ go up dramatically in the ipsalateral hemisphere compared to the levels in the contralateral hemisphere. See the bars marked as vinblastine. When rats are depleted of neutrophils by vinblastine treatment, 0.5 mg/kg IV, prior to experimental TBI, leukotriene production in the ipsalteral hemisphere is markedly reduced. The reduction of leukotrienes by vinblastine is seen only in the ipsilateral hemisphere where the blood-brain barrier has been compromised. Data represent 4-5 animals per group. Results are the average±SEM. **$P<0.01$.

Figures 3A, 3B:
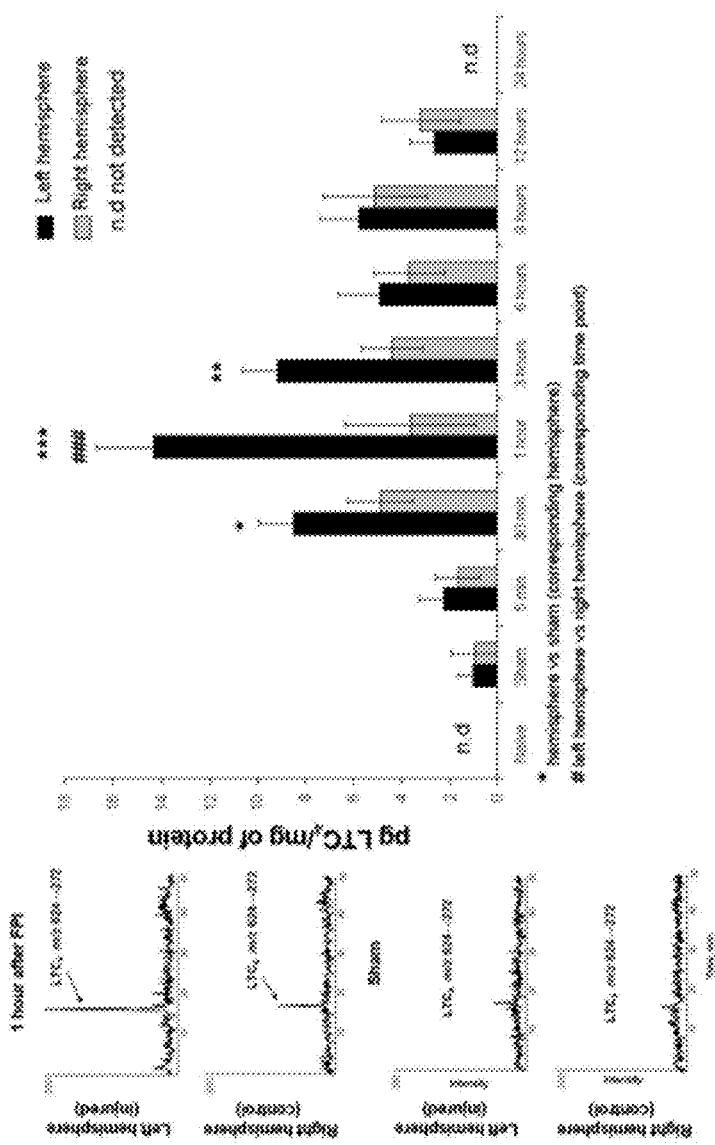
FIG. 3A shows the $LTC_4$ levels in the ipsalateral and contralateral hemispheres of a sham-treated and a TBI treated animal 1 hour after fluid percussion injury.
FIG. 3B shows the time course of $LTC_4$ synthesis in left and right brain hemispheres of naïve, sham, and head-injured animals after TBI.

FIG. 3A shows the $LTC_4$ levels in the ipsalateral and contralateral hemispheres of a sham treated and a FPI treated animal 1 hour after treatment as measured by RP LC-MS/MS. The results show that the sham treated animal had very little $LTC_4$ and that there are no differences between the right and left hemisphere. The results for the FPI treated animal shows that there is a dramatic increase in the level of $LTC_4$ in both the ipsalateral and contralateral hemispheres. The increase in the ipsalateral hemisphere is much higher than that in the contralateral hemisphere.

FIG. 3B shows the time course of $LTC_4$ synthesis in left and right brain hemispheres of naïve, sham, and head-injured animals after TBI. Leukotrienes were measured by reverse-phase chromatography coupled to tandem mass spectrometry (RP-LC/MS/MS), $LTC_4$ and $LTD_4$ are undetectable in the naïve, uninjured, brain. Levels of $LTC_4$ in sham animals are not significantly different from uninjured animals. After experimental TBI by FPI leukotrienes are rapidly produced. Levels of $LTC_4$ are 4-fold higher in the ipsilateral, left, brain hemisphere compared to the contralateral, right, brain hemisphere (14.35+/−2.31 pg/mg protein vs. 3.624+/−2.73 pg/mg protein). Similar results are obtained for $LTD_4$ (not shown) consistent with the metabolism of $LTC_4$ to $LTD_4$ by neuronal tissue. Data represent 4-5 animals per group. Results are the average±SEM. Significant difference from homologous hemisphere of sham-injured animals. (*P<0.001; P<0.01; *P<0.005). Significant difference from contralateral hemisphere (***P<0.001).

Figures 4, 5:
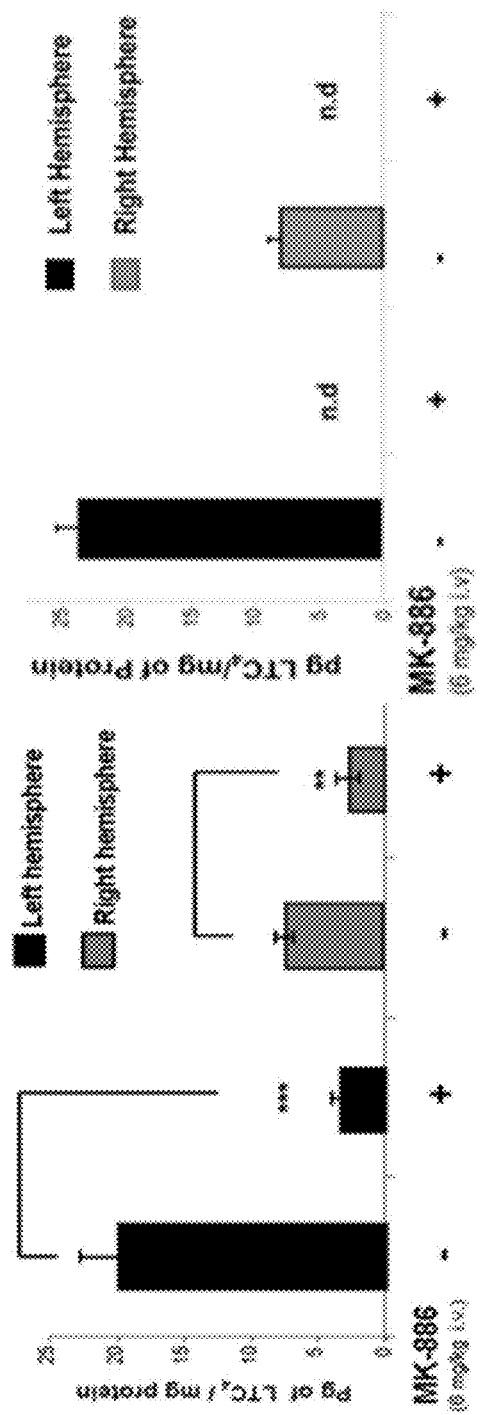
FIG. 4 shows that administration of the FLAP inhibitor MK-886 prior to TBI markedly reduces leukotriene $LTC_4$ production in both brain hemispheres.
FIG. 5 shows that administration of the FLAP inhibitor MK-886 15 minutes after TBI completely blocks injury-induced leukotriene $LTC_4$ synthesis.

The results from FIG. 3B indicate that injury-induced leukotriene production is very rapid, peaking at 1-3 hours after TBI and declining to undetectable levels by 24 hours. To determine the efficacy of pre- and post-injury MK-886 administration in blocking leukotriene formation, rats were injected with a single dose of either MK-886 at 6 mg/kg in 0.9% sterile saline with 10% DMSO or the same volume of vehicle 30 minutes before or 15 minutes after TBI. At time points after injury, the animals were euthanized and the levels of $LTC_4$ were measured in brain regions after extraction of lipids and analysis by RP LC-MS/MS. Animals administered a single-dose of MK-886 at 6 mg/kg, IV by tail vein 30 minutes prior to TBI showed significant reductions in leukotriene production 1 hour after TBI. $LTC_4$ levels in the ipsilateral left hemispheres of MK-886-treated injured animals were 85% lower than levels in vehicle-treated injured animals. The level in vehicle treated animals was 20.00+/−2.71 pg/mg protein versus 3.39+/−0.42 pg/mg protein in MK-886-treated animals. $LTC_4$ levels in the contralateral right hemispheres of MK-886-treated injured animals were also lower by 64% than vehicle-treated injured animals. The level in vehicle-treated was 7.19+/−0.63 pg/mg protein versus 2.6+/−0.80 pg/mg protein in MK-886 treated animals. FIG. 4, shows that administration of the FLAP inhibitor MK-886 30 minutes prior to TBI markedly reduces leukotriene $LTC_4$ production in both brain hemispheres. Animals administered a single-dose of the FLAP inhibitor MK-886, 6 mg/kg IV by tail vein, 30 minutes prior to FPI show significant reductions in leukotriene production measured 1 hour after injury. Four-five animals were used in each group. Results are the average SEM. (*P<0.001 P<0.01).

In another experiment rats received a single-dose of MK-886 15 minutes after the TBI. The mean $LTC_4$ level in the ipsilateral hemisphere 23.41+/−1.98 pg/mg protein was significantly higher (p<0.001, student's t-test) than the contralateral hemisphere 7.92+/−1.02 pg/mg protein of vehicle-treated animals. Administration of MK-886 15 minutes after the TBI reduced the levels of $LTC_4$ to below the detectable threshold in both the ipsilateral and contralateral hemispheres. FIG. 5 shows that administration of the FLAP inhibitor MK-886 15 minutes after TBI blocks injury-induced leukotriene synthesis to below detectable levels. Quantitative analysis of $LTC_4$ levels in the ipsilateral and contralateral hemispheres in rats injected with either vehicle (−) or MK-886(+) 15 minutes after injury are shown in FIG. 5. The results show that MK-886 administered 15 minutes after TBI completely blocked the rise in $LTC_4$ expected following a TBI. After treatment with MK-886 there was no detectable $LTC_4$. Values are mean+/−SEM, non-detectable. *p<0.05, different from ipsilateral hemisphere, student's t-test.

To investigate the relative amount of $LTC_4$ production in injured ipsilateral cortex and hippocampus, these brain regions were dissected from injured rats prior to RP LC-MS/MS analysis, $LTC_4$ was detected in both the ipsilateral cortex, 9.67+/−1.18 pg/mg protein and the hippocampus, 6.05+/−3.70 pg/mg protein, of vehicle-treated animals. Similar to results in whole brain hemispheres, $LTC_4$ was undetectable in ipsilateral cortex and hippocampus of MK-886-treated animals. These results along with those of FIG. 4 demonstrate that the FLAP inhibitor, MK-886, effectively blocks leukotriene biosynthesis when administered 30 minutes before or 15 minutes after experimental TBI.

Figure 6:
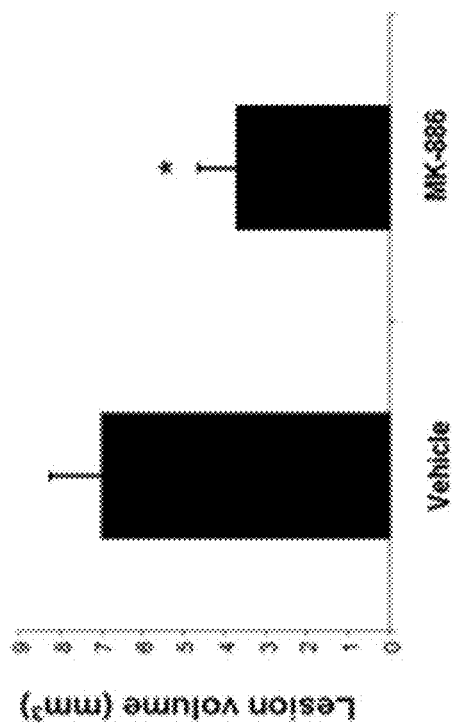
FIG. 6 shows that pre-treatment with the FLAP inhibitor MK-886 30 minutes before the TBI reduces the volume of cell death measured 72 hours after TBI.

FIG. 6 shows that administration of the FLAP inhibitor MK-886 reduces the volume of cell death determined 72 hours after TBI. Rats were administered a single-dose of the FLAP inhibitor MK-886, 6 mg/kg IV by tail vein, 30 minutes prior to TBI. The pre-treated animals show significant reductions in cell death induced by TBI when measured 72 hours later. Results are expressed as the average±SEM. Significant difference from vehicle treated animals (*P<0.05).

In another experiment T2-weighted MRI was used to investigate the effect of leukotrienes on TBI-related brain edema 72 hours after TBI in rats. The rats were injected with MK-886 either 30 minutes before, 15 minutes after or 60 minutes after TBI. Additional groups of sham-injured and vehicle-injected animals were used as controls. The ipsilateral left and contralateral right brain hemispheres of sham animals showed no T2-weighted hyperintensity and were symmetrical in height and width. In contrast, the brains from TBI-injured animals consistently demonstrated T2-weighted hyperintensity and unilateral swelling in the ipsilateral hemisphere compared to the contralateral hemisphere.

Ipsilateral hemispheric edema was quantified relative to the contralateral hemisphere. Sham animals exhibited no difference between hemispheres in normalized brain swelling (0.00+/−0.03%). In contrast, injured animals given vehicle treatment had significantly more brain swelling than sham animals, vehicle=8.68+/−0.09%, p<0.001, one-way ANOVA followed by Tukey's HSD. Animals receiving MK-886 either 30 minutes pre-injury, or 15 min post-injury had significantly lower swelling than vehicle-treated animals. For 30 minutes pre-TBI the value was 4.12+/−0.08%, p=0.004; for 15 minutes post-TBI it was 426+/−0.05%, p=0.028. Animals injected with MK-886 60 min post-TBI did not significantly differ from vehicle-treated animals, 60 minutes post-TBI value was 8.98+/−1.0%, p=0.999. These results demonstrate that blocking leukotriene production either before or shortly after TBI reduces the amount of injury-related brain swelling at 72 hours.

Figure 7:
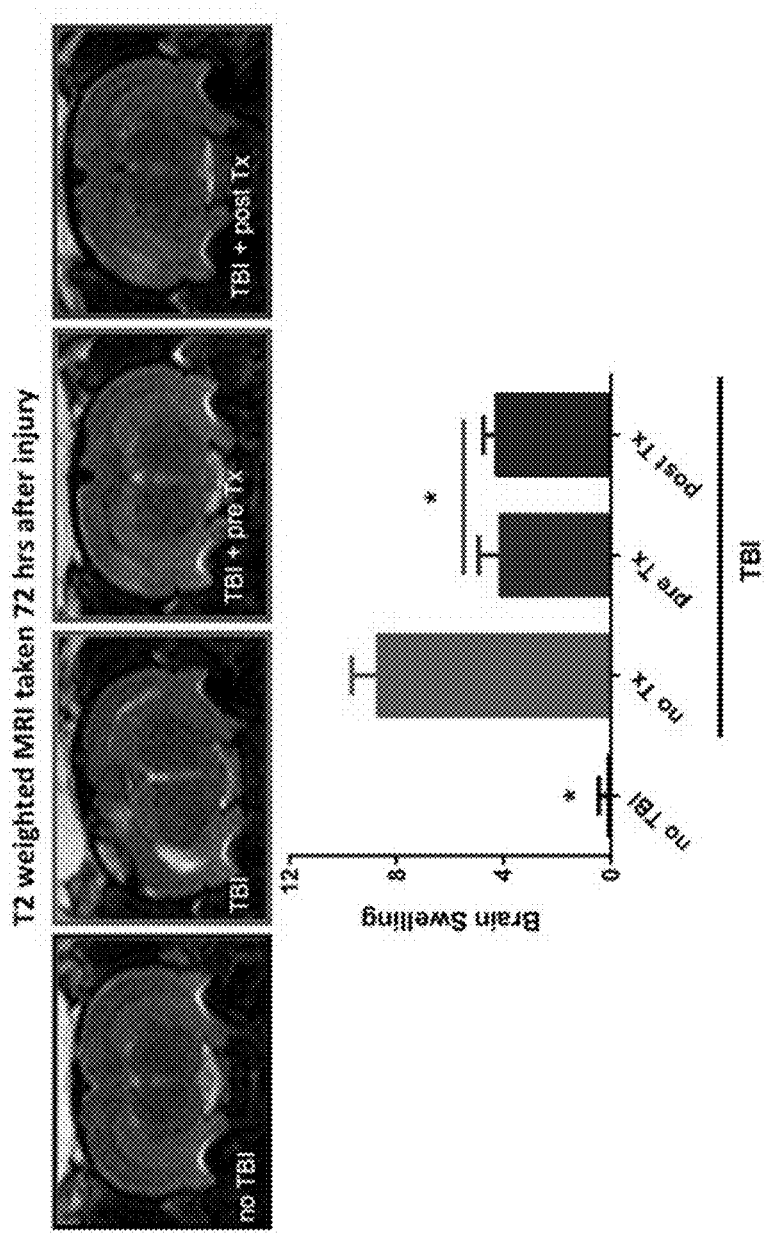
FIG. 7 top panel shows that the FLAP inhibitor MK-886 administered either before or after TBI attenuates edema after TBI, representative T2-weighted MRI images obtained 72 hours after FPI, bottom figure shows quantitative MRI analysis of the mean normalized brain swelling calculated from 5 continuous T2-MRI slices obtained from each animal group using Fiji (NIH)

FIG. 7 shower that the FLAP inhibitor MK-886 attenuates edema when administered either 30 minutes pre-TBI or 15 minutes after TBI in rats. The top panel of images are representative T2-weighted MRI images obtained 72 hours after a TBI event. The ipsilateral, left, and contralateral, right, hemispheres in the sham, no TBI, brain show no T2 pixel hyperintensity and are symmetric in shape and size.

Brains from TBI treated animals demonstrate T2 pixel hyperintensity primarily in the ipsilateral cortex indicative of water content and unilateral swelling. Quantitative MRI analysis of the mean normalized brain swelling was calculated from 5 continuous T2-MRI slices obtained from each animal using Fiji (NIH). Values are mean+/−SEM, Sham (n=4), Vehicle (n=8), MK-886 administered 30 minutes pre-injury (n=10), and 15 minutes post-injury (n=5). Bar=5 mm. The results show that MK-886 administered either 30 minutes before or 15 minutes after a TBI significantly reduced the brain swelling when compared to TBI treated with no MK-886. *p<0.05, different from vehicle TBI group, not significantly different from sham, one way ANOVA, followed by Tukey's HSD.

The effect of leukotrienes on TBI-related BBB disruption was assessed using Gd-enhanced T1-weighted MRI 72 hours after TBI in rats. The rats were intravenously injected with the contrast-enhancing agent, Gd, which deposits in brain regions where the BBB has been compromised and registers on T1-weighted MRI scans. Gd extravasation, detected by the increase in pixel hyperintensity in the post-Gd images, was detected exclusively in the ipsilateral leptomeningeal region (surface) of TBI-injured animals. The presence of Gd in this region is most likely due to the mechanical shearing of blood vessels in this highly vascularized region of the brain. The total volume of Gd extravasation, post-Gd pixel hyperintensity, in each animal was quantified. The TBI increased Gd extravasation, and MK-886 had no effect when administered 30 min pre-injury (p=419), 15 min post-injury (p=0.970) or 60 min post-injury (p=0.994) (one-way ANOVA followed by Tukey's HSD). Although MK-886 had no apparent effect on Gd extravasation, regulation of the BBB permeability by leukotrienes may be masked by the mechanical injury to blood vessels at the surface of the brain.

The inventors utilized Evans Blue (EB) fluorescence to assess BBB permeability in the rat FPI model. EB (<1 kDa) is an azo dye that has a strong affinity for serum albumin (67 kDa). The resulting EB-albumin complex leaks into the parenchyma upon disruption of the BBB. Fluorescence microscopy was used to image brain slices harvested five hours post-injury, taking advantage of EB's intrinsic fluorescent properties, excitation at 620 nm and emission at 680 nm. This method is more sensitive than commonly used colorimetric readings of EB in brain homogenates, Uyama O, *J. Cerebr. Blood F. Met.* 8, 2827-284, 1988, and can be used to localize BBB permeability. As the EB-albutnin complex is taken up by cells proximal to sites of permeability, this method allows for microscopic detection of BBB disruption. Consistent with this, the brightest EB signal co-localized with 4',6-dimidino-2-phenylindole (DAPI) fluorescence, indicating dye uptake by cells. Faint extracellular fluorescence was also observed surrounding EB-positive cell clusters. Not unexpectedly, the greatest density of EB-positive cells was in the ipsilateral cortex adjacent to the injury site and in the ipsilateral hippocampus, with some scattered cells in the thalamus and substantia nigra. There was no EB detected in the corresponding contralateral brain regions. Since the hippocampus is relatively distant from the primary injury site and mediates memory and learning processes, the inventors counted EB-positive cells in hippocampus as a measure of parenchymal BBB disruption. MK-886 administered 15 minutes after TBI significantly reduced the number of EB-positive cells in the CA1 region. The value for TBI vehicle-treated was 148.75+/−45.65 while the value for TBI MK-886 treated was 69.25+/−36.82, p=0.035, student's t-test. These results indicate that leukotrienes can mediate BBB permeability in selective brain regions vulnerable to injury and that FLAP inhibitors block leukotriene-mediated BBB disruption.

Figures 8A, 8B, 8C:
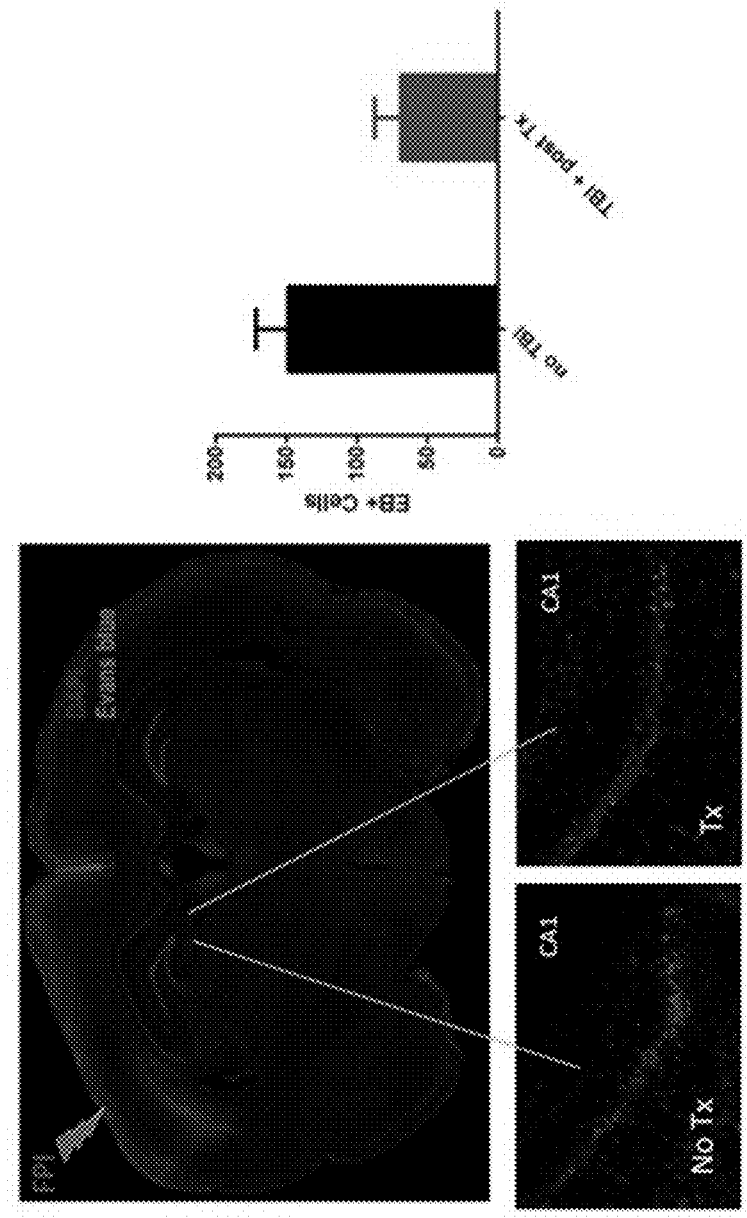
FIGS. 8A, 8B, and 8C show that administration of the FLAP inhibitor MK-886 30 minutes after TRI reduces BBB permeability in the CA1 region of hippocampus.

FIGS. 8A, 8B and 8C show that administration of the FLAP inhibitor MK-886 30 minutes after TBI in the rat FPI model reduces BBB permeability in the CA1 region of hippocampus. FIG. 8A is a representative fluorescence image of EB (red) uptake by hippocampal cell layers and DAPI uptake (blue) in the ipsilateral hippocampus 5 hours after TBI. FIG. 8B is a higher magnification of images of EB extravasation in the ipsilateral CA1 hippocampal cell layer in animals that received either vehicle or MK-886 15 minutes after TBI. FIG. 8C is a graph showing quantitation of EB+ cells, EB-DAPI colocalization, in the hippocampal regions. Bar=200 μm. Values are mean+/−SEM; n=4. *p<0.05, student's t-test. Similar results were obtained when the FLAP inhibitor was administered 30 minutes prior to injury, data not shown.

To examine the functional integrity of the hippocampus after TBI, electrophysiological measurements of long-term potentiation (LTP) were recorded in rat hippocampal slices four days after TBI by the FPI model. The LTP is a measure of synaptic plasticity and is thought to represent the molecular mechanisms underlying learning and memory. Synaptic field excitatory post-synaptic potential (fEPSP) responses were evoked by stimulating the CA3 to CA1 Schaffer collateral pathway and recording from the CA1 dendritic field layer. There was no difference in the fEPSP input-output curves (F(4,381)=0.5329, p=0.992, two-way repeated measures ANOVA), nor in the paired pulse ratio measurements between sham and TBI-injured animals, (T(22)=1.883, p=0.073, student's t-test), indicating similar levels of basal synaptic transmission for these groups. This is consistent with the inventors' previous findings that there was no substantial hippocampal cell loss by H&E staining and no change in the levels of hippocampal neurofilament protein within one week of TBI. Hippocampal slices from sham animals exhibited robust LTP in response to high frequency stimulation (253.51+/−69.48%, 58-60 min, last 3 recorded time points). In contrast, hippocampal slices from uninjected TBI-injured animals failed to express LTP (135.06%+/−42.62%, different from sham animals, p=0.007 one-way ANOVA of all groups followed by Tukey's HSD). Similar to the uninjected TBI-injured animals, hippocampal slices from TBI-injured animals injected with vehicle also failed to exhibit LTP upon high frequency stimulation. However, animals that received an injection of MK-886 either 30 minutes before or 30 minutes after TBI demonstrated normal LTP. Both were significantly different from vehicle-injected animals. The TBI vehicle value was 130.86%+/−55.63%; TBI with MK-886 30 minutes pre-injury value was 242.75+/−76.94%, p=0.032; and TBI with MK-886 30 minutes post-injury value was 256.13+/−8.527%, p=0.007, one-way ANOVA followed by Tukey's HSD. However, when MK-886 was delivered 60 minutes post-injury, the drug failed to prevent the LTP deficits observed in vehicle-treated animals, value 145.46+/−18.30, p=0.994. These results indicate that blocking early production of leukotrienes attenuates injury-induced deficits in animal hippocampal synaptic plasticity after injury and suggests a time window of less than one hour after injury for efficacy of MK-886 treatment in rodents which likely translates to a window of 2-3 hours post-injury in humans.

Figure 9:
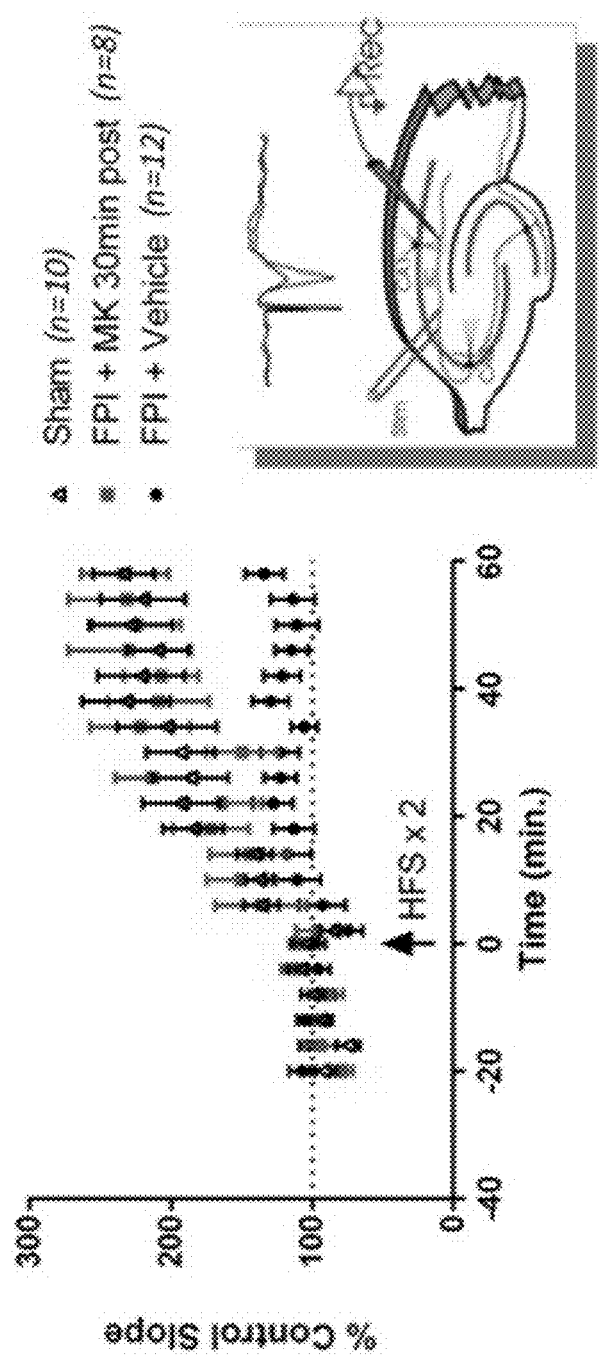
FIG. 9 shows that administration of the FLAP inhibitor MK-886 30 minutes after TBI attenuates deficits in hippocampal long-term potentiation after TBI, LTP measured in hippocampal slices from sham rats (open triangles, n=8) and FPI-injured rats injected with vehicle (closed circles, n=7) or MK-886 30 minutes after FPI (red squares, n=7), data are represented as a % of the control fEPSP slope, each data point shown is an average of six 20-s interval measurements, sham n=8, FPI n=9, inset depicts a representative sham fEPSP.

FIG. 9 shows that administration of the FLAP inhibitor MK-886 30 minutes after TBI in the rat FPI model attenuates deficits in hippocampal long-term potentiation (LTP) after TBI. The LTP was measured in hippocampal slices from sham rats (open triangles, n=8) and FPI-injured rats injected with vehicle (closed circles, n=7) or MK-886 30 minutes after FPI (red squares n=7). The average LTP response (mean+/−SEM control slope) in all the groups measured at 58-60 minutes after induction of LTP. $*p<0.05$, $**p<0.01$, different from FPI vehicle, not significantly different from sham, sane-way ANOVA followed by Takey's HSD.

To verify that TBI induced deficits in LTP reflect impairments in hippocampal-dependent spatial learning and memory, sham and TBI-injured rats treated with drug or vehicle were tested in a radial arms water maze (RAWM) four and five days after TBI. The RAWM has an advantage over the Morris water maze in assessing cognitive impairments in rodents, in that the number of entries into an arm lacking the escape platform can be used as an assessment of learning, rather than latency to find the platform, thereby eliminating confounds induced by potential differences in swim velocities among the experimental groups. Sham and TBI-treated animals received an injection of either vehicle or MK-886 30 minutes post-injury. On the first day of behavioral testing, the animals completed 15 swim trials in which they used visual cues to navigate the maze to find a hidden escape platform in one of the arms, this arm is called the goal arm. There were no significant differences in initial task learning between the vehicle and MK-886 treated animals within the sham group or within the TBI group ($F(3,155)=2.437$, $p=0.083$, two-way repeated measures ANOVA) and no significant differences between groups for any cluster of 3 swims, (one-way ANOVA for each swim cluster). On the second day of behavioral testing, animals completed five swim trials in the maze with the goal arm in the same position as the previous day. The escape platform was then moved to a new location for ten more trials in order to assess the ability of the animals to learn and remember a new goal arm location, the reversal task. In the first three trials of the reversal task, perseverance for the previous goal arm was measured as the percent of total swim duration spent in the arm where the platform used to be. On the first swim, there were no differences in perseverance between any of the groups ($F(3,31)=0.713$, $p=0.522$ one-way ANOVA). Both sham groups quickly learned between swims 1 and 3 that the platform was no longer in the previous goal arm. Likewise, TBI rats treated with MK-886 spent less time in the previous goal arm by swim 3 (overall interaction, injury (sham v. FPI)×drug (MK-886 v. vehicle)× trial (swim one to swim three), $F(1,62)=5.564$, $p=0.025$, within subjects two-way repeated measures ANOVA followed by student's paired t-test, sham vehicle, $p=0.001$; sham MK-886, $p=0.006$; FPI MK-886, $p=0.035$). However, TBI animals that received a vehicle injection failed to learn that the platform location had changed between swims 1 and 3 ($p=0.758$). The last five swim trials of the reversal task (swims 6-11) were used for assessment of continued learning. Vehicle-treated TBI rats continued to make significantly more errors per swim than sham animals given either drug or vehicle (TBI vehicle=2.33+/−1.21; sham vehicle=0.755+/−0.705, $p=0.003$; sham MK-886=0.850+/−0.583, $p=0.005$; one-way ANOVA followed by Tukey's HSD). The TBI animals given MK-886 did not differ from either sham group and were significantly different from TBI-vehicle animals (1.26+/−0.700, $p=0.044$). These data indicate that MK-886 attenuates TBI injury-induced deficits in spatial learning and memory.

Figure 10:
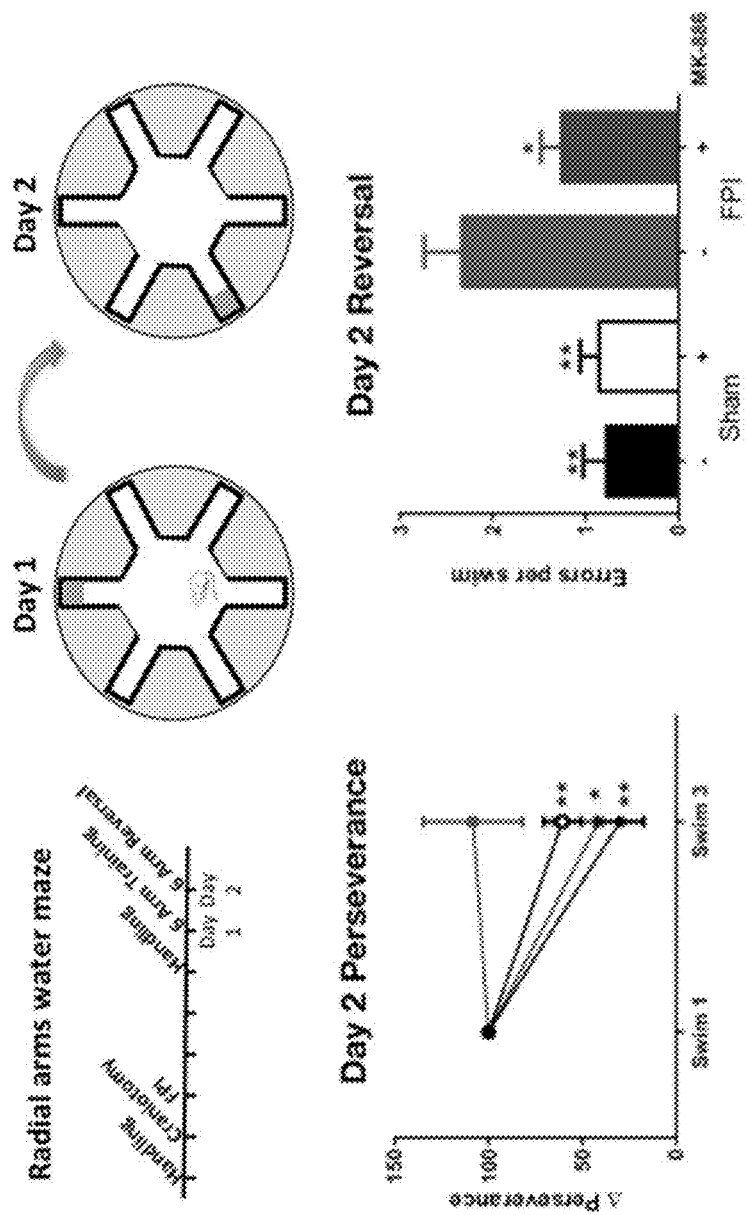
FIG. 10. The FLAP inhibitor MK-886 administered 30 min after TBI mitigates TBI-induced impairments in memory and learning in radial aims water maze in a Day 2 reversal task perseverance test measured as the change in perseverance, duration in previous goal arm, at swim 3 expressed as the percentage of perseverance in swim 1 and Day 2 reversal task performance errors (mean±SEM) made in swims 11-15 of the reversal task.

FIG. 10 shows that the FLAP inhibitor MK-886 administered 30 minutes after TBI mitigates TBI-induced impairments in memory and learning in radial arms water maze in the rat FPI model. In the Day 2 reversal task perseverance the change in perseverance, duration in previous goal arm, at swim 3 is expressed as the percentage of perseverance in swim 1. $*p<0.05$, $**p<0.01$, within-subjects two-way repeated measures ANOVA followed by paired student's t-test, Day 2 reversal task performance as errors (mean+/−SEM) made in swims 11-15 of the reversal task. $*p\leq0.05$, $**p<0.01$, different from FPI vehicle, no difference from either sham group, one-way ANOVA followed by Tukey's HSD.

Figure 11:
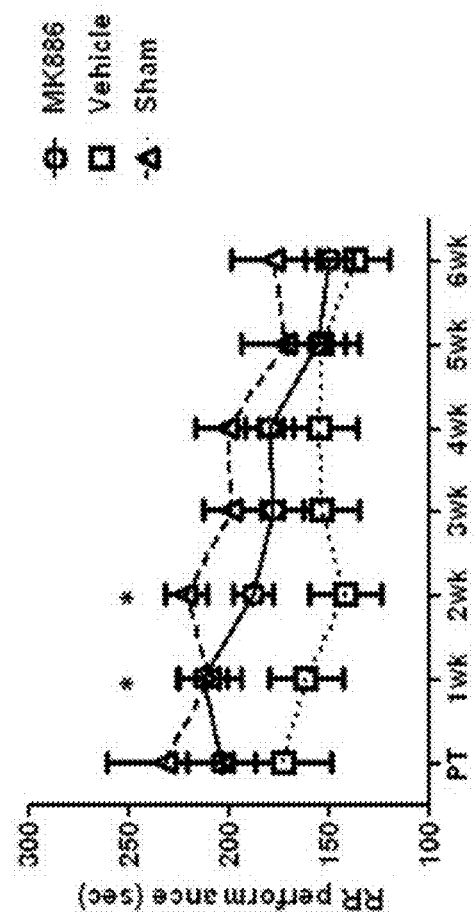
FIG. 11 shows the FLAP inhibitor MK-886 mitigates motor deficits caused by TBI when administered 15 minutes after TBI as shown by improved vestibulomotor performance on the rotarod.

The results shown in FIG. 11 demonstrate that the FLAP inhibitor MK-886 mitigates motor deficits after TBI in the rat FPI model. When MK-886 was administered 15 minutes after TBI the animals had improved vestibulomotor performance on the rotarod compared to the vehicle treated animals. For rotarod testing, the rod's rotation was programmed to accelerate from 0 to 50 rpm over the course of 300 seconds. Four trials were run at each selected time point after injury and the individual trial and mean times for each animal are recorded. PT is pre-injury training. Values are mean+/−SEM. n=6-9. The results show that the MK-886 treated animals had a better response thatn those seem with vehicle treated animals during weeks 1 and 2. Eventually, all the groups came to the same relative performance.

Figure 12:
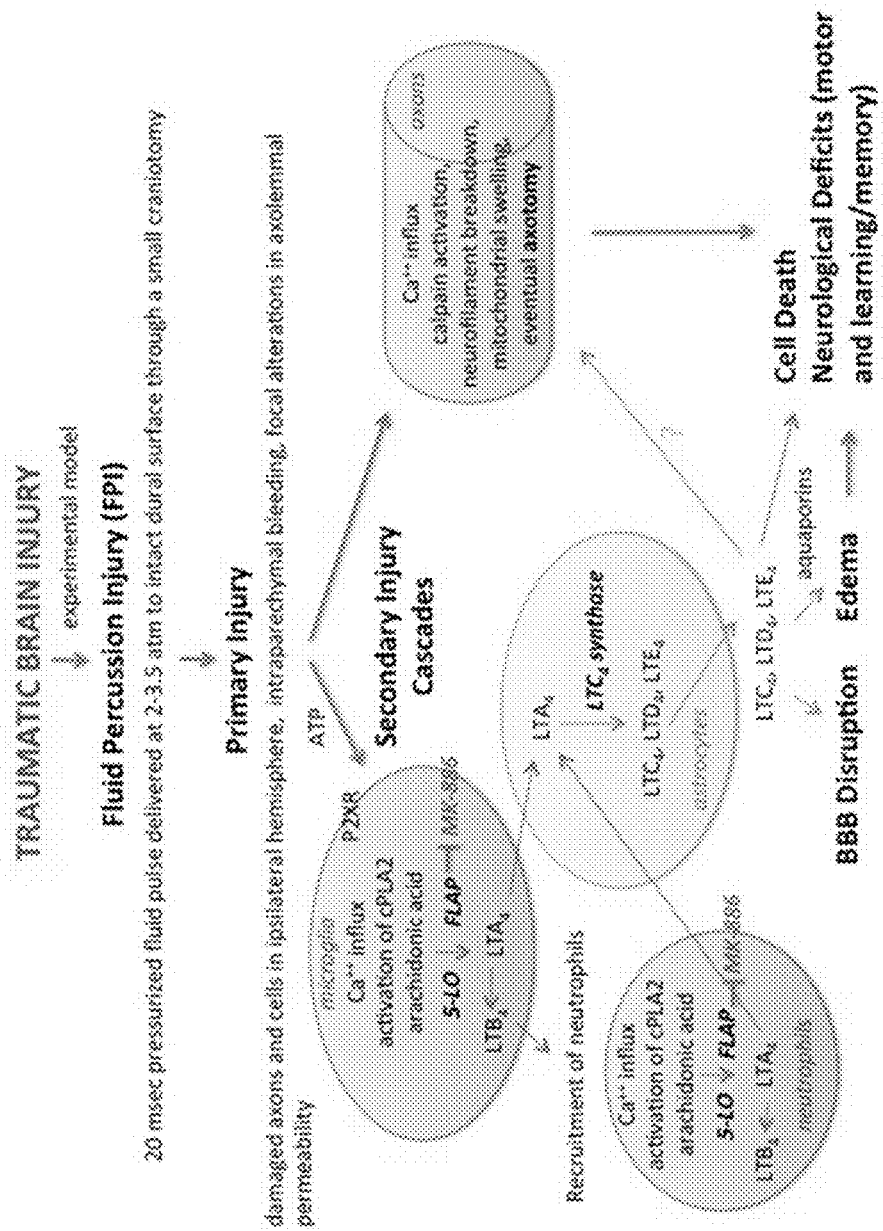
FIG. 12 is a summary and schematic of a proposed connection between leukotrienes and TBI in the FPI model according to the present invention.

FIG. 12 is a summary and schematic of a proposed connection between leukotrienes and TBI according to the present invention based on the results discussed above with respect to the FPI model. While not being bound to this theory, based on the current evidence presented in this invention, the following sequence of events occurs after TBI. The primary brain injury at the time of the trauma results in ATP leakage from damaged cells into the extracellular space, intraparechymal bleeding and focal alterations in axolernmal permeability. Following release, the ATP binds to microglia causing calcium influx and activation of cytosolic phospholipase A2 (cPLA$_2$), which releases AA from membrane phospholipids. The AA is converted to 5-HETE and then to LTA$_4$ by 5-LO and FLAP. The LTA$_4$ is then converted either to LTB$_4$, a potent chemotactic molecule that recruits neutrophils, by LTA$_4$ hydrolase or it is transported out of microglia and taken up by neighboring astrocytes and possibly neurons that make the cys-LTs (LTC$_4$, LTD$_4$, and LTE$_4$) through the action of LTC$_4$-synthase. The early production of leukotrienes signals adverse effects including leukocyte infiltration, BBB disruption, and edema. The latter effect appears to be mediated by aquaporin water channels. If unchecked, these detrimental events lead to further axonal injury, cell death, motor deficits, and cognitive impairments.

Figure 13:
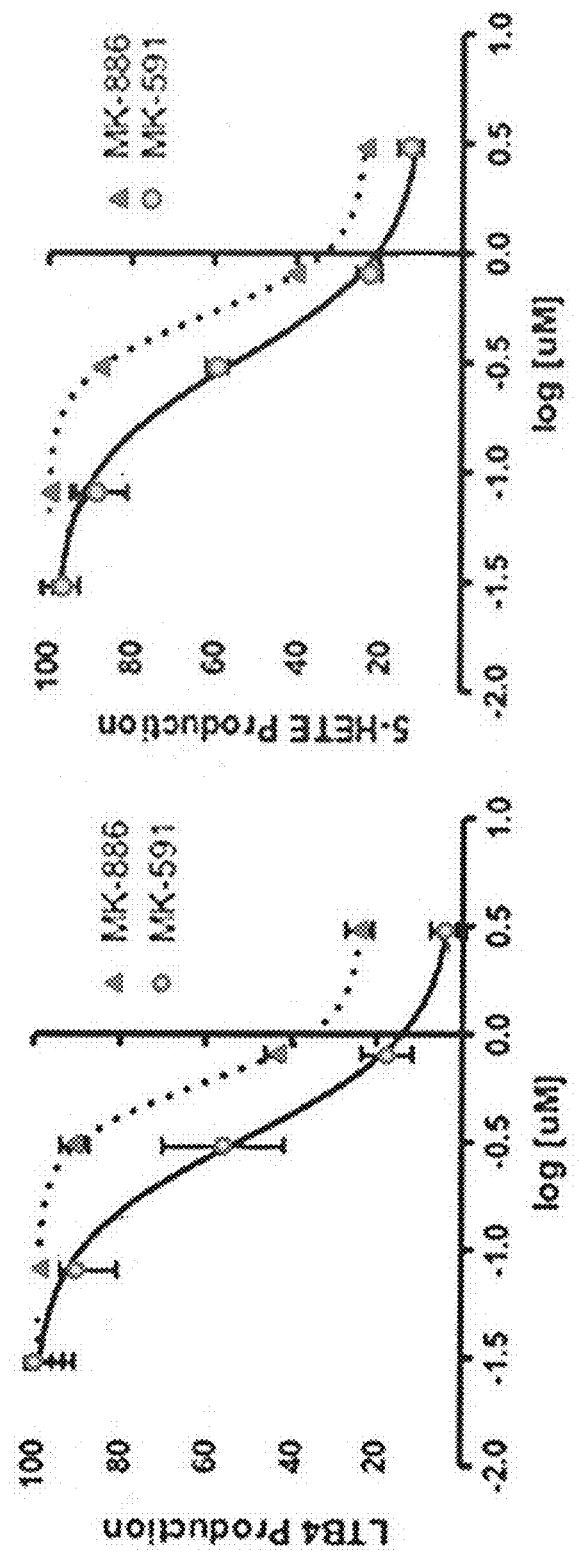
FIG. 13 shows a comparison of the potency of MK-886 in the solid triangles and MK-591 in the solid circles, in human whole blood oar LTB4 production and 5-HETE production.

FIG. 13 shows a comparison of the in vitro potency of MK-886, solid triangles dotted line, and MK-591, solid circles solid line in human whole blood. The results are for the effects of these two FLAP inhibitors on LTB$_4$ production and 5-HETE production. It is known that indole-acetic acid FLAP inhibitors like MK-886, MK-591 display high plasma protein binding. Thus, the potencies of these FLAP inhibitors for blocking leukotrienes in vivo are about 100 fold higher than the affinity of the inhibitors for FLAP binding. The inventors developed a bioassay that closely predicts the in vivo potency of FLAP inhibitors using human whole blood. Briefly, whole blood is incubated with a calcium ionophore like A2387 or zymosan in the absence or presence of increasing concentrations of a FLAP inhibitor. After incubation at 37° C. for 30 minutes, the samples are centrifuged and the plasma supernatant is subjected to reverse phase liquid chromatography coupled to tandem mass spectrometry to quantify levels of LTB$_4$, 5-HETE, and AA production. Drug $IC_{50}$ values are determined by non-linear regression analysis (GraphPad Prism).). The results demonstrate that the MK-886 and MK-591 FLAP inhibitors had the expected and reported IC50 in the presence of protein. As expected neither of the FLAP inhibitors effected AA production, data not shown. As FLAP inhibitors are poorly water soluble drugs, the inventors have shown that such hydrophobic drugs can be formulated in a carrier comprising one or more vegetable oils, such as olive oil, and phosphatidylserine that are found on the Generally Accepted as Safe (GRAS) list and that such drugs can then be rapidly delivered and targeted to the brain and upper spinal cord. Hanson L R, et al, Drug Delivery 19(3):149-54, 2012.

Figure 14:
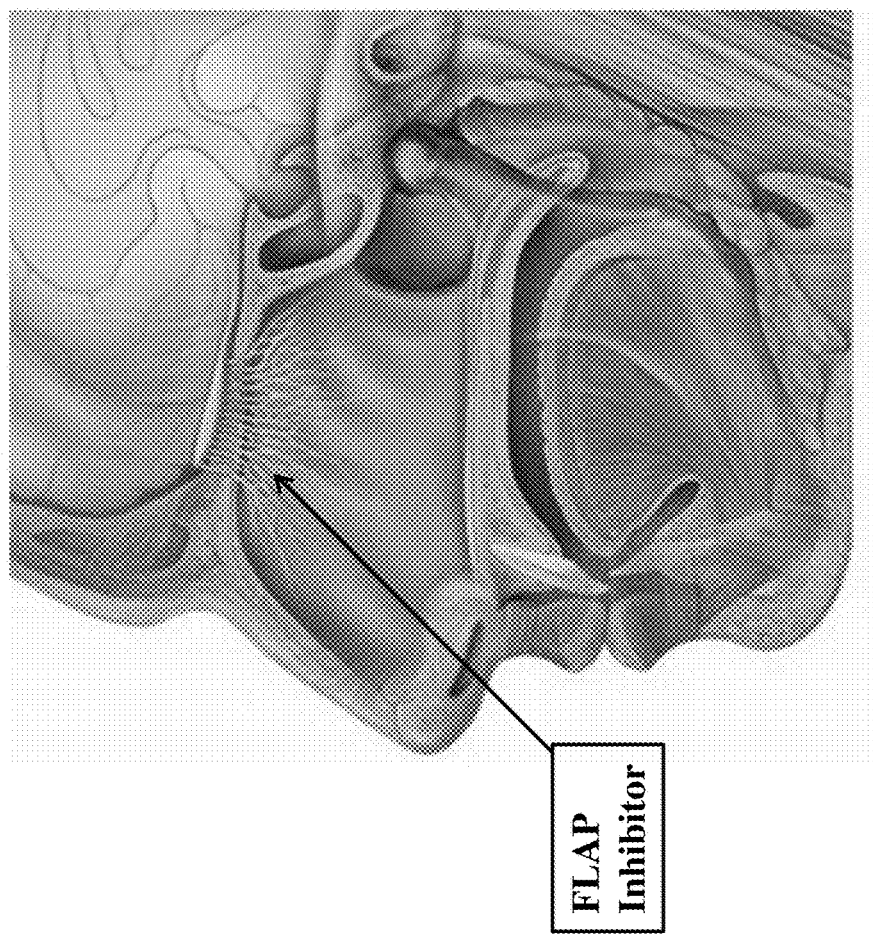
FIG. 14 is a schematic showing an example of intranasal delivery of FLAP inhibitors.

The data described above was generated using IV or IP injections of the FLAP inhibitors into rats. FIG. 14 shows a schematic of a method of intranasal delivery of FLAP inhibitors. Intranasal drug delivery bypasses the BBB, by delivering drugs directly from the nasal mucosa to the brain and upper spinal cord along the trigeminal and olfactory neural pathways via an extracellular mechanism, thereby increasing brain bioavailability. Intranasal drug administration limits the amount of drug entering the systemic circulation thus decreasing the potential for undesirable adverse systemic consequences such as for example liver and heart toxicity of a pharmacologic agent. The delivery of drugs is very rapid via this route, reaching the brain within 10 minutes, a factor critical for TBI intervention as shown by the data above, and the method of nasal delivery is quick and simple making it very suitable to a wide variety of settings.

Figure 15:
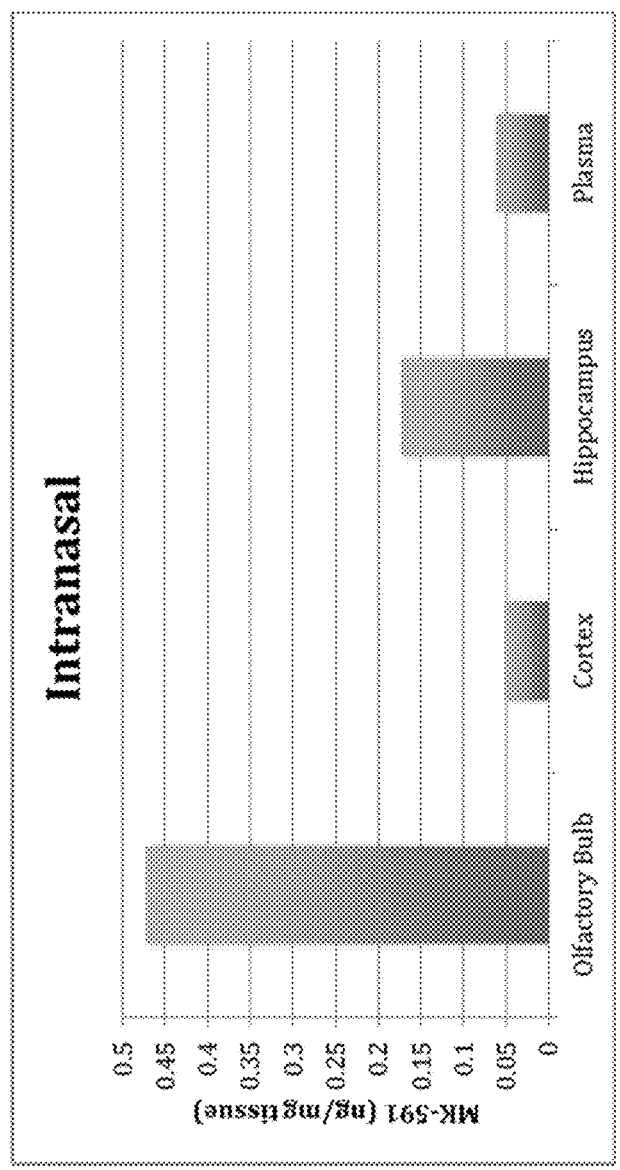
FIG. 15 shows brain localization of the FLAP inhibitor MK-591 in several regions versus the plasma level at 30 minutes after intranasal administration of the MK-591.

The FLAP inhibitor MK-591 is more potent and has a longer $t_{1/2}$ than MK-886. The MK-591 was formulated in a lipid carrier solution as described above. FIG. 15 shows brain localization of the FLAP inhibitor MK-591 in several rat brain regions versus the plasma level at 30 minutes after intranasal administration of the MK-591. The rats were briefly anesthetized with 3.5% isoflurane and intranasal MK-591 (60 micrograms/32 ul lipid carrier) was administered in eight 4 ul aliquots to the nasal mucosa alternating between each nostril. The amount of drug was determined with the goal of reaching 200 nM concentration of drug which corresponds to 100× the Kd value for binding to FLAP. At 30 minutes post-dosing, blood was collected from anesthetized animals using a heparanized needle and plasma was separated from blood by centrifugation. The animals were then perfused with saline, while still under anesthesia, to remove drug in the blood of the cerebrovasculature. After perfusion the animals were euthanized and brain regions were rapidly removed. Both plasma and brain tissue samples were frozen in liquid nitrogen followed by storage at −80° C. Drug levels in the peripheral plasma and parenchymal brain tissues were assessed using a validated tandem mass spectroscopy platform. Values are expressed in ng of MK-591/mg tissue. The highest level of MK-591 was detected in the olfactory bulbs, followed by the hippocampus, and cortex. The concentration of MK-591 in the cortex was 200 nM, the target concentration. The levels of drug in plasma were lower than the amount of drug reaching the brain. These results demonstrate that intranasal delivery of the FLAP inhibitor MK-591 is possible and that physiologically relevant levels are rapidly achieved in a variety of brain regions.

Figure 16:
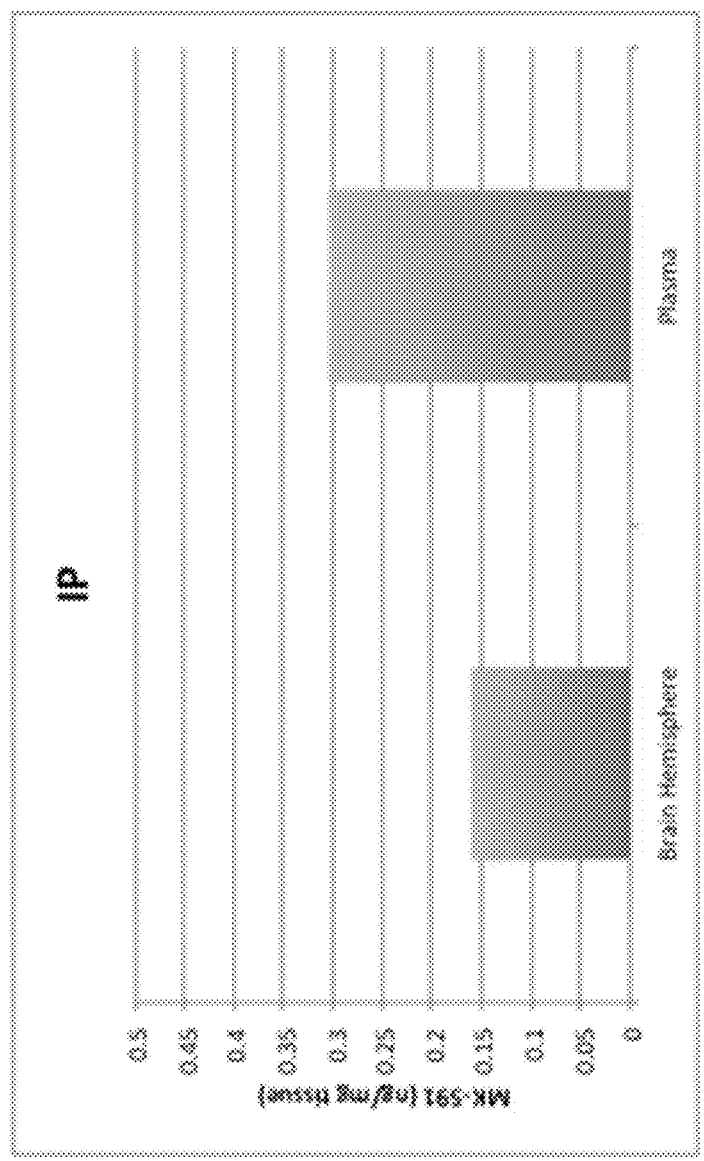
FIG. 16 shows brain and plasma levels of the FLAP inhibitor MK-591 at 30 minutes after intraperitoneal administration.

FIG. 16 shows rat brain hemisphere and plasma levels of the FLAP inhibitor MK-591 at 30 minutes after intraperitoneal administration. The rats were injected intraperitoneally with MK-591 (10 mg/kg in 20% DMSO/saline solution). At 30 minutes post-dosing, blood was collected from anesthetized animals using a heparanized needle and plasma was separated from blood by centrifugation. The animals were then perfused with saline, while still under anesthesia, to remove drug in the blood of the cerebrovasculature. After perfusion the animals were euthanized and brain hemispheres were rapidly removed. Both plasma and brain tissue samples were frozen in liquid nitrogen followed by storage at −80° C. Drug levels in the peripheral plasma and brain were assessed using a validated tandem RP-LC/MS/MS platform. Unlike, the intranasal method, most of the drug was in the plasma with much lower levels found in brain tissue. Using the conversion of 1 ml=1 gm. The total volume of blood was 2 ml (or 2 mg). The total weight of the brain hemisphere (minus cerebellum) is 0.150 mg. Values are expressed in ng of MK-591/mg tissue. These results demonstrate the value of intranasal delivery versus IP administration in terms of rapidly delivering FLAP inhibitors to the TBI effected areas to have a maximal effect.

Figure 17A:
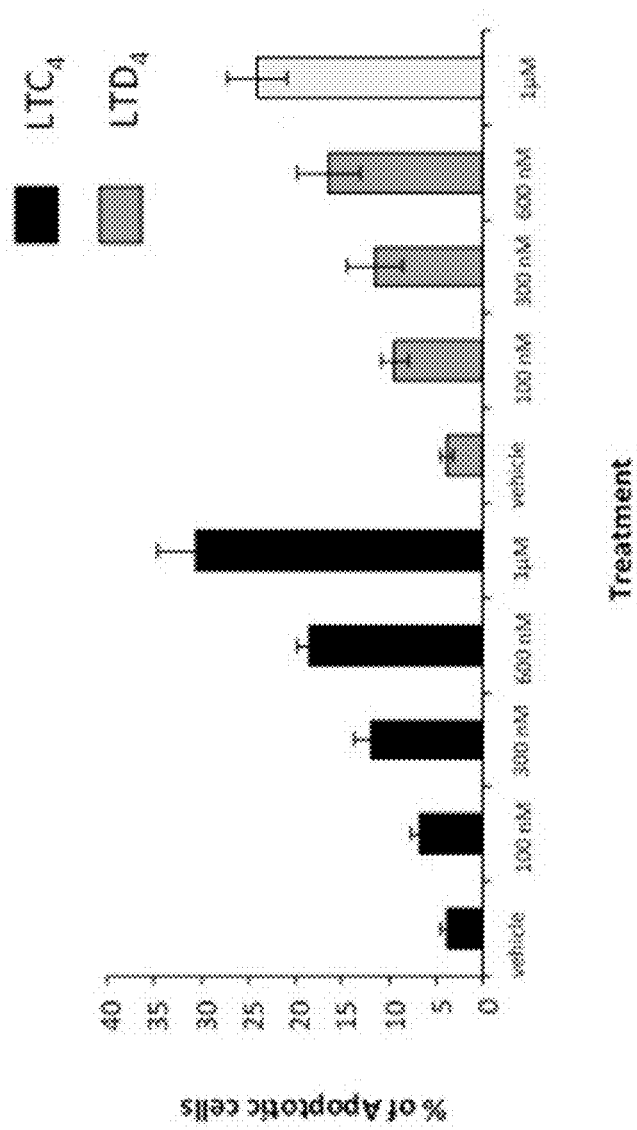
FIG. 17A shows that the leukotrienes $LTC_4$ and $LTD_4$ induce neuronal apoptosis, programmed cell death, in vitro in a dose-dependent manner.
Figure 17B:
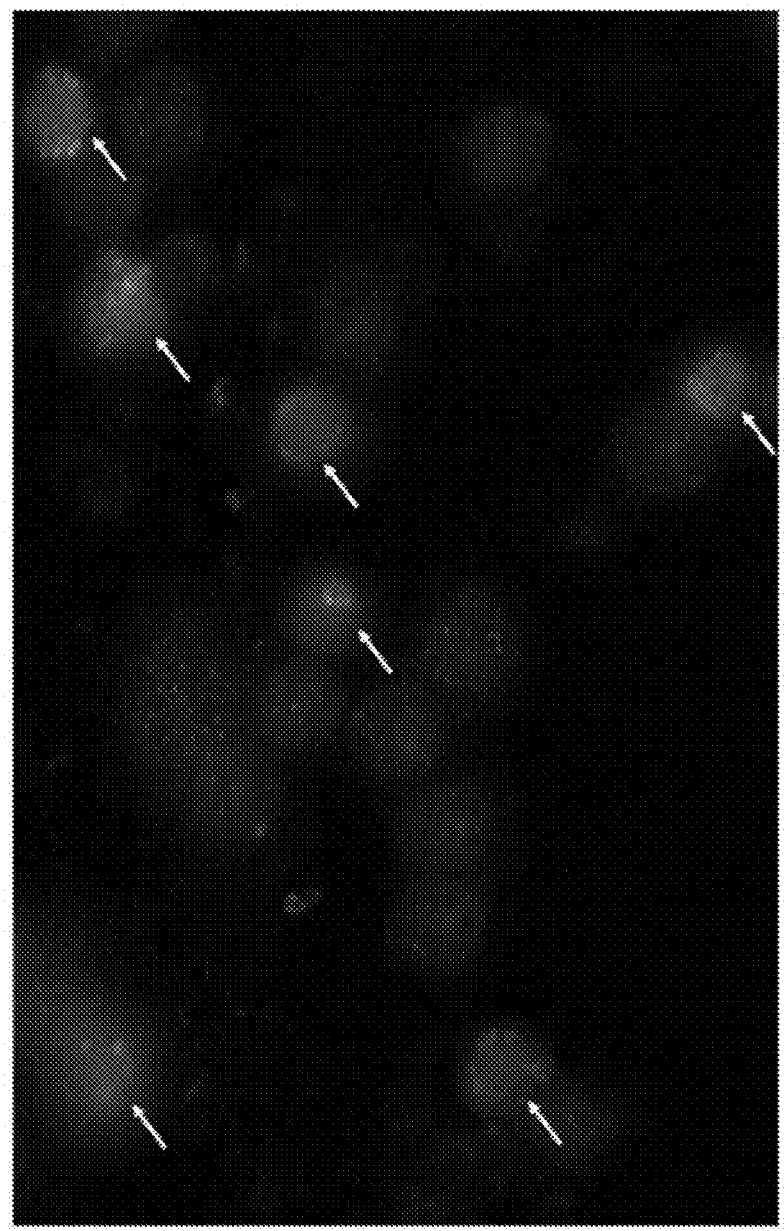
FIG. 17B shows cells stained with DAPI and an antibody to active-caspase 9 (arrows) to verify that the neurons were dying by intrinsic apoptosis.

The results of FIGS. 17A and 17B demonstrate that the leukotrienes $LTC_4$ and $LTD_4$ induce neuronal apoptosis, programmed cell death, in vitro in a dose-dependent manner. Primary neurons cultured from newborn rats were incubated in the presence of increasing concentrations of $LTC_4$ or $LTD_4$ for 16 hours. The number of apoptotic neurons was determined by counting the number of DAPI-stained neurons that showed nuclear condensation and expressed as percent of total neurons. Neurons were also stained with antibodies against active-caspase 9 (arrows) to determine if neurons were dying by intrinsic apoptosis. Results indicated that the leukotrienes induced intrinsic apoptosis of neurons. These data are in agreement with recent reports that leukotrienes, in addition to their inflammatory effects, stimulate β-amyloid production by regulating secretase activity, β-amyloid is know to kill neurons by inducing apoptosis. These results taken together with the data above indicate that leukotrienes have both pro-inflammatory and direct neurotoxic actions in the brain.

Experimental Results Mouse CHI Model

Figure 18:
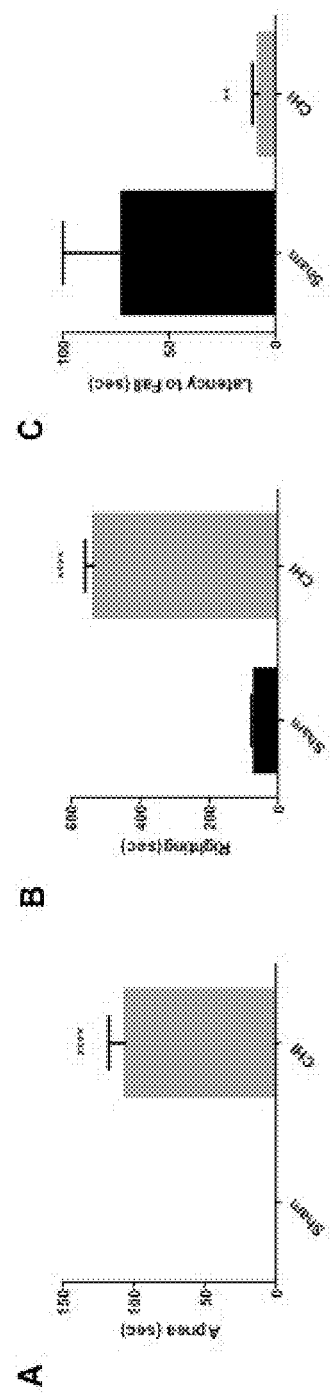
FIG. 18 panels A, B, and C show comparisons between sham operated mice and mice in a mouse closed head injury (CHI) model in terms of their apnea, righting reflex, and latency to fall measures as confirmation of a traumatic brain injury.

In a second species, the mouse, another TBI model was tested to confirm and extend the results reported above. In the mouse closed head injury (CHI) model an electromagnetically controlled piston is used to deliver a mild TBI to the subject animal, the exact process used is described above in the experimental protocols section. In a first series of tests the effect of the CHI on three measures of injury severity was determined. The three measures are apnea, righting time, and latency to fall. The apnea and righting reflex measures were done immediately after the CHI process. The apnea measure is the time it takes a subject to start breathing on its own following the CHI while the righting time is the time it takes for the subject to regain the righting reflex of going from laying on their side to standing on all four limbs. The combination of apnea and righting reflex are comparable to a loss of consciousness in humans following TBI. The latency to fall mesures were conducted 1 hour after the CHI and measures the length of time that a subject can grip and hang from a wire mesh before falling. The results are shown in FIG. 18, panels A-C. In panel A the apnea measures are presented, as expected the sham mice had no apnea while the CHI mice had an average apnea measure of over 100 seconds. Similarly, the righting reflex in the sham mice was very short while the CHI mice had an average of over 500 seconds, an increase of over 7 fold. With respect to the latency to fall, the CHI mice had a much shorter latency to fall, indicating that their grip strength had been reduced. The sham operated mice could hang on for over 7 fold longer than the CHI mice. The results demonstrate that the mice subjected to the CHI protocol exhibit all the signs of a mild TBI (mTBI) event and validate the protocol. The numbers and degree of significance were as follows: apnea measure **p<0.0001 sham n=29 CHI n=66; righting reflex p<0.0001 sham n=29 CHI n=66; latency to fall p<0.0056 sham n=29 CHI n=66.

Figure 19:
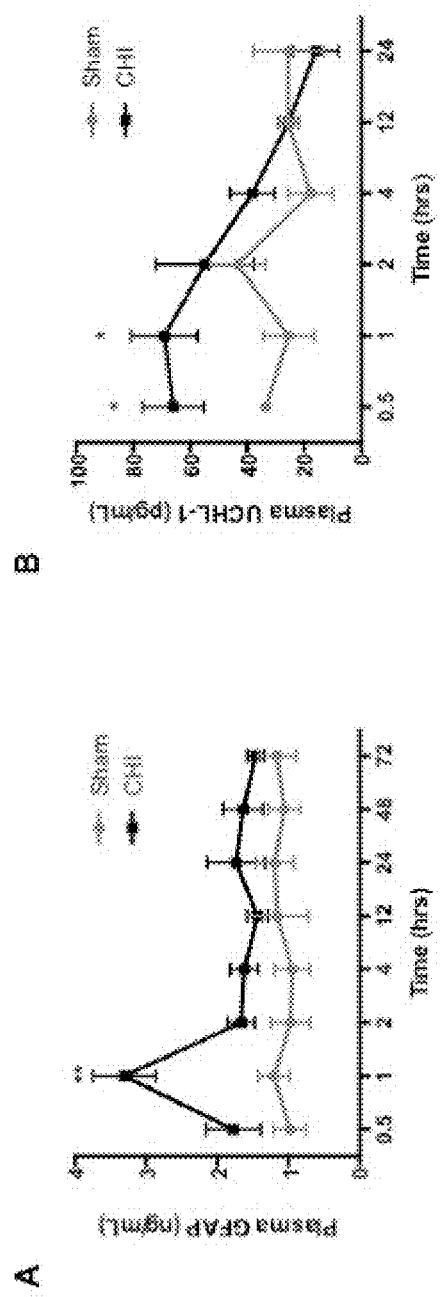
FIG. 19 panels A and B show comparisons between the plasma levels of two markers for mild TBI in sham operated mice and in mice from a mouse closed head injury (CHI) model, the levels were measured at the noted times after injury, the markers are glial fibrillary acidic protein (GFAP) in mg/ml and ubiquitin carboxy-terminal hydrolase L-1 (UCHL-1) in pg/ml.

Using the CHI model a series of mice were sham operated or CHI treated and then at time intervals following treatment the mice were anesthetized and blood samples were collected by cardiac puncture using a 22 gauge needle. The samples were placed in hepranized microcentrifuge tubes. The plasma was prepared by centrifugation of the whole blood at 7,000 rpm for 15 minutes and stored in the same tubes at −80° C. until analyzed using commercially available Elisa kits. The two biomarkers followed in the plasma were glial fibrillary acidic protein (GFAP) and ubiquitin carboxy-terminal hydrolase L-1 (UCHL-1). These two are associated with human mTBI events, the GFAP is an indicator of astrocyte cell death while the UCHL-1 is associated with neuronal cell death. The results for GFAP are shown in FIG. 19 panel A and show that the levels as expected are steady in the sham mice. The CHI mice show a peak GFAP level at 1 hour post injury and the levels return to basal levels within 12 hours post injury. The CHI mice also show elevated levels of UCHL-1 that are maximal by 2 hours post injury and back to basal levels by 2 hours post injury, FIG. 19 panel B. These measures further confirm that the CHI model is producing the expected mTBI in the subject mice. The sham n=3-5 mice per time point, the CHI n=4-9 per time point. The significance at 1 hour for GFAP was **p=0.0014. The significance for the 0.5 hour value of UCHL-1 was *p=0.0193 and at 1 hour it was **p=0.0223.

Figure 20:
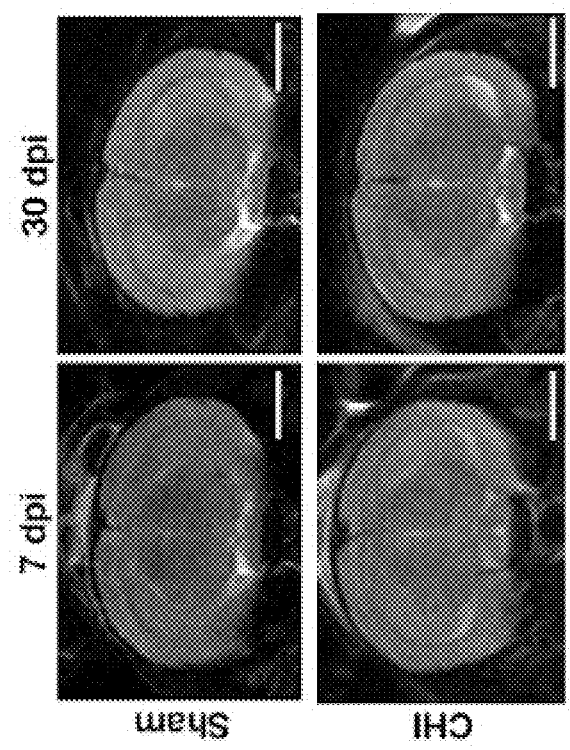
FIG. 20 shows representative images of T2-weighted Magnetic Resonance Images from sham operated mice and from mice in a mouse closed head injury (CHI) model at 7 and 30 days post injury (dpi), scale bar is 2 mm, no edema was detected.

To evaluate the edema caused by the CHI protocol mice were either sham operated or CHI treated and then 7 dpi or 30 dpi they were subjected to T2 weighted MRI. None of the mice, either sham or CHI, showed any T2-weighted pixel hyperintensity at any time after CHI indicating that there was no edema further validating that this is an appropriate mTBI model. The absence of a positive MRI is also common in the majority of human cases of mTBI. FIG. 20 shows representative MRI images from sham operated and CHI mice at 7 and 30 dpi, scale bar is 2 mm.

To examine the neuroinflammation following CHI mice were subject to the CHI protocol and then various brain regions were stained for reactivity to H&E, myeloperoxidase (MPO) a marker of neutrophils, GFAP a marker of reactive astrocytes, and Iba-1 a marker of activated microglia.

Figure 21:
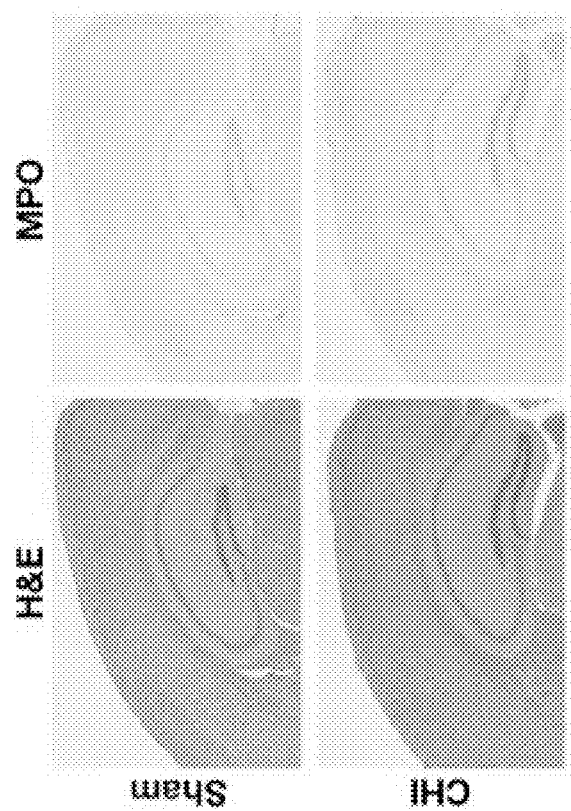
FIG. 21 shows representative images of brain sections from sham operated mice and from mice in a mouse closed head injury (CHI) model stained histochemically for H&E at 7 dpi and immunohistochemically for myeloperoxidase (MPO) 30 dpi.

FIG. 21 shows representative examples of the results of staining for H&E at 7 dpi or for MPO at 30 dpi in sham and CHI mice. At all time points examined the results showed no evidence of any lesions nor did they show any evidence of neutrophil infiltration in the regions. There were no contusions or cell losses by H&E staining or significant blood brain barrier disruption as assessed by MPO staining. The lack of overt damage after the CHI in the mice mimics what is typically seen in human studies of mTBI. No overt brain damage of infiltrating immune cells was detected in this model in contrast to the FPI model. In human studies the is generally no gross pathology, such as a contusion or hemorrhage, by either CT or conventional MRI scans. The results are consistant with the CHI being a good model for mTBI in humans.

Figure 22:
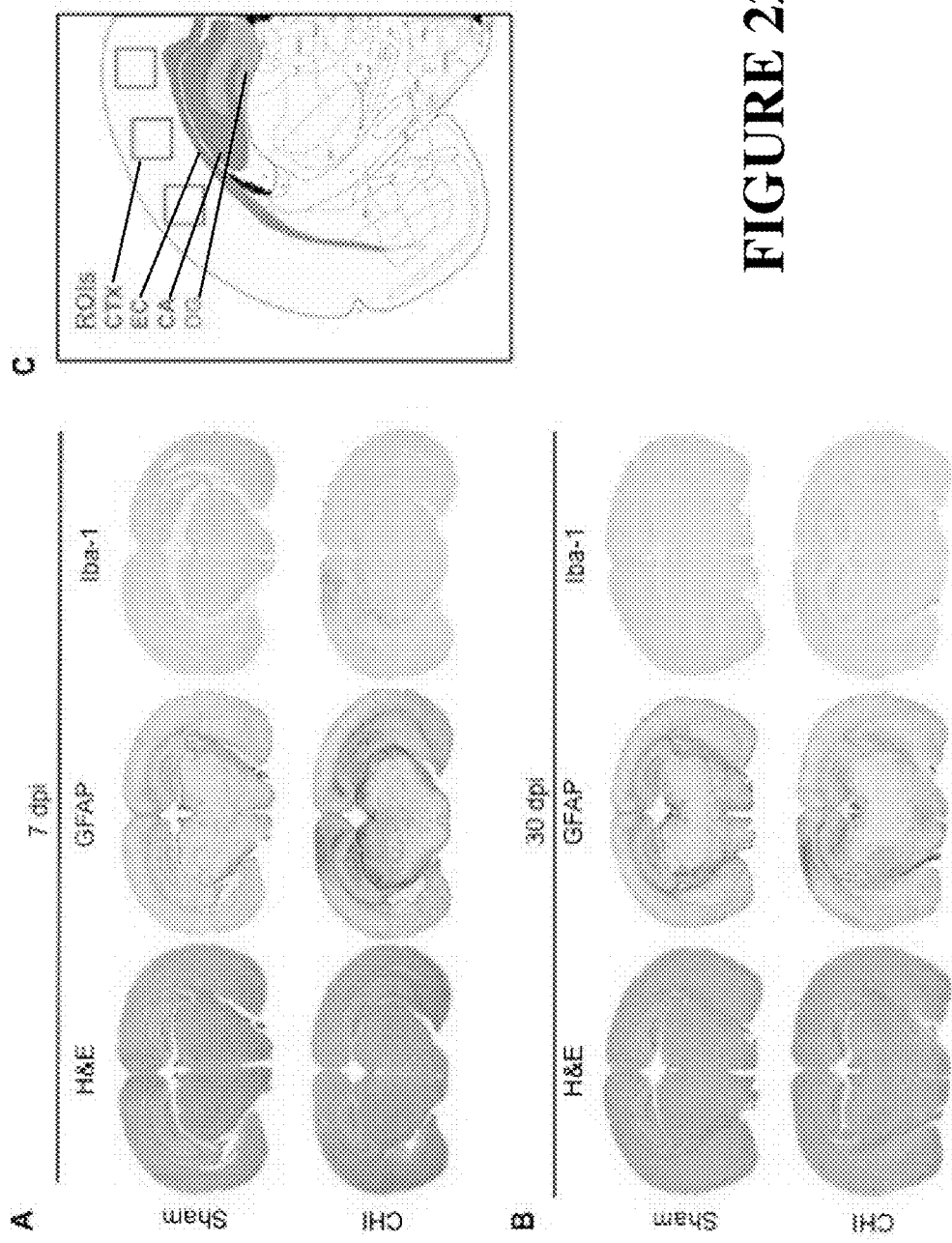
FIG. 22 panels A and B show representative images of coronal brain sections from sham operated mice and from mice in a mouse closed head injury (CHI) model stained histochemically for H&E, immunohistochemically for GFAP, and immunohistochemically for ionized calcium-binding adapter molecule 1 (Iba-1) at 7 days and 30 dpi, respectively, FIG. 22 panel C is a schematic of a coronal cross section of mouse brain that shows regions of the brain that are of special interest, namely the cerebral cortex (CTX), external capsule (EC), CA region of the hippocampus, and dentate gyms (DG)

In contrast to the absence of macroscopic changes in the brains of CHI mice at the microscopic level there were large scale changes indicative of neronalinfiammation. FIG. 22 panels A and B show representative coronal brain slices stained for H&E, GFAP, or Iba-1 in sham and CHI mice at 7 and 30 dpi. FIG. 22 panel C shows regions of interest including: cerebral cortex (CTX), external capsule (EC), CA region of the hippocampus, and dentate gyrus (DG). The regions showing the highest reactivity to GFAP and Iba-1 after the CHI were the CTX, EC and DG, As shown in FIG. 22 panels A and B there was significant staining for GFAP at both 7 and 30 dpi in the CHI mice compared to the sham mice. The largest amount of staining, as expected, is on the ipsilateral hemisphere to the CHI. The regions of CTX, EC and DG are critical for executive type brain functions, learning, and memory. The EC is a large white matter tract that contains corticocortical association fibers that are responsible for connecting one cortex of the brain to other and it is a route for cholinergic fibers from the basal forebrain to the cerebral cortex. This region of the brain also shows structural alterations by diffusion tensor imaging after mTBI in humans. The DG is a sub-region of the hippocampus that mediates neurogenesis and is critical for learning and memory. Neural progenitor cells in the sub annular zone of the dentate gyrus produce new neurons throughout adulthood. Recent studies in humans using radiocarbon dating techniques indicate that neurogenesis occurs at significant levels, about 1,400 new granule neurons are added daily throughout adulthood. These newborn granule neurons play an essential role in memory pattern separation and impairments in neurogenesis are thought to contribute to anxiety disorders by impairing memory generalization. Such impairments could underlie the pathological fear responses seen in anxiety disorders such as post-traumatic stress disorder and panic disorder. Thus, neuroinflammation in the dentate gyms as shown in the present invention may provide a mechanistic link between TBI and PTSD.

Figure 23:
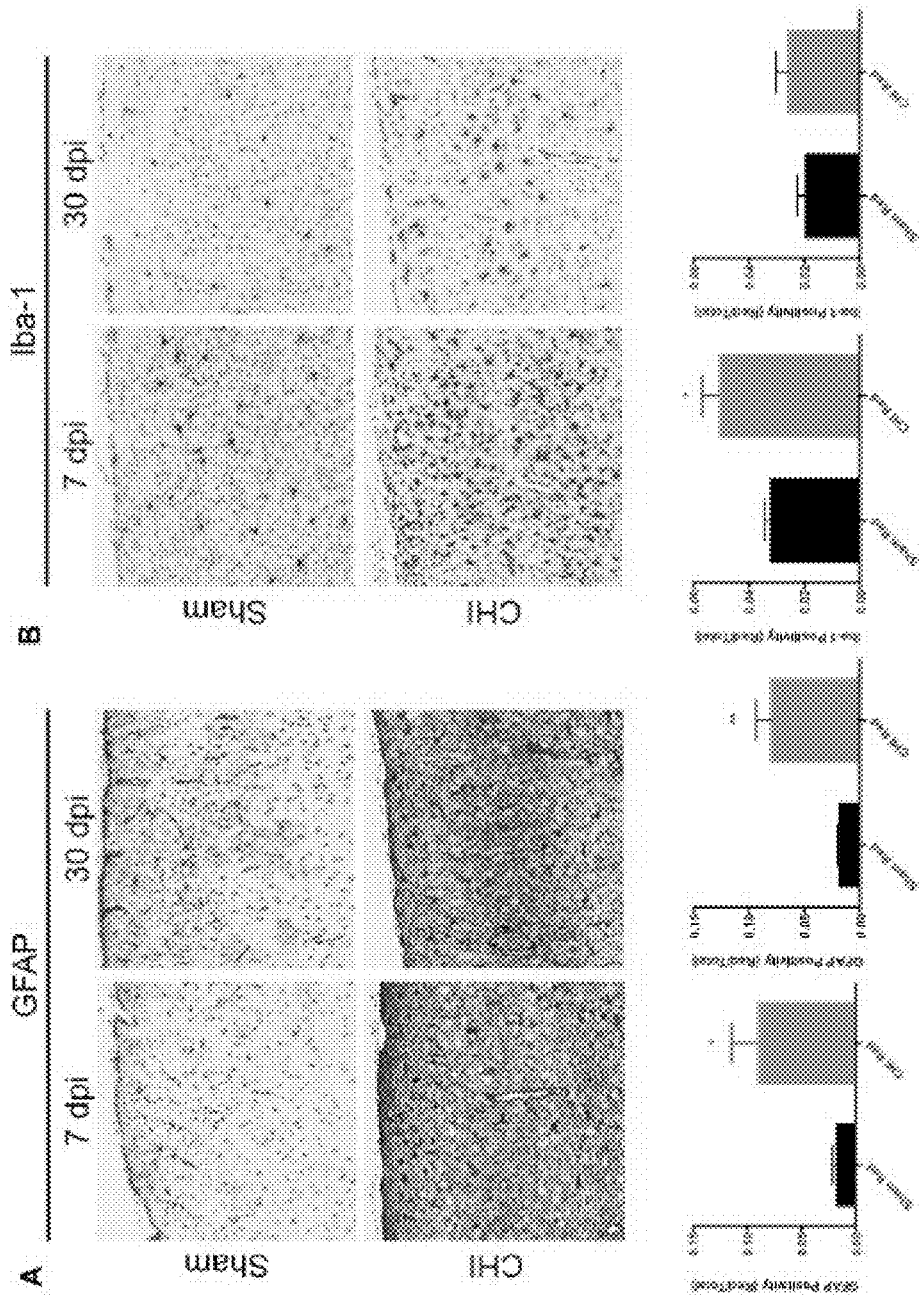
FIG. 23 panels A and B show representative images of cortical brain sections from sham operated mice and from mice in a mouse closed head injury (CHI) model stained immunohistochemically for GFAP at 7 and 30 dpi and immunohistochemically for ionized calcium binding adapter molecule 1 (Iba-1) at 7 and 30 dpi, respectively, also shown below the representative stained sections are graphs showing the quantitative analysis of similar sections at 7 dpi on the left and at 30 dpi on the right for the same markers.

FIG. 23 panel A shows representative staining for GFAP in the cortex of sham and CHI mice at 7 and 30 dpi and below the representative samples there is quatitiative analysis of the results from multiple mice. The representative sections show a dramatic increase in GFAP in the CHI mice that is sustained for at least 30 dpi. The quantitative results show significant increases in measured GFAP positivity at 7 and 30 dpi. The numbers and significance were: 7 dpi sham n=7 CHI and *p=0.0188; 30 dpi sham n=7 and CHI n=11 **p=0.0021. FIG. 23 panel B shows representative staining for Iba-1 in the cortex of sham and CHI mice at 7 and 30 dpi and below the representative samples there is quatitiative analysis of the results from multiple mice. The representative sections show a dramatic increase in Iba-1 in the CHI mice that is very high after 7 dpi and still elevated after 30 dpi, The quantitative data show that at 7 dpi there is a significant increase in the Iba-1 reactivity of the CHI mice. There is still an elevation at 30 dpi, but it was not statistically significant in this study. The numbers and significance were as follows: 7 dpi sham n=6 and CHI n=7 *p=0.0233; at 30 dpi sham n=7 and CHI n=9.

Figure 24:
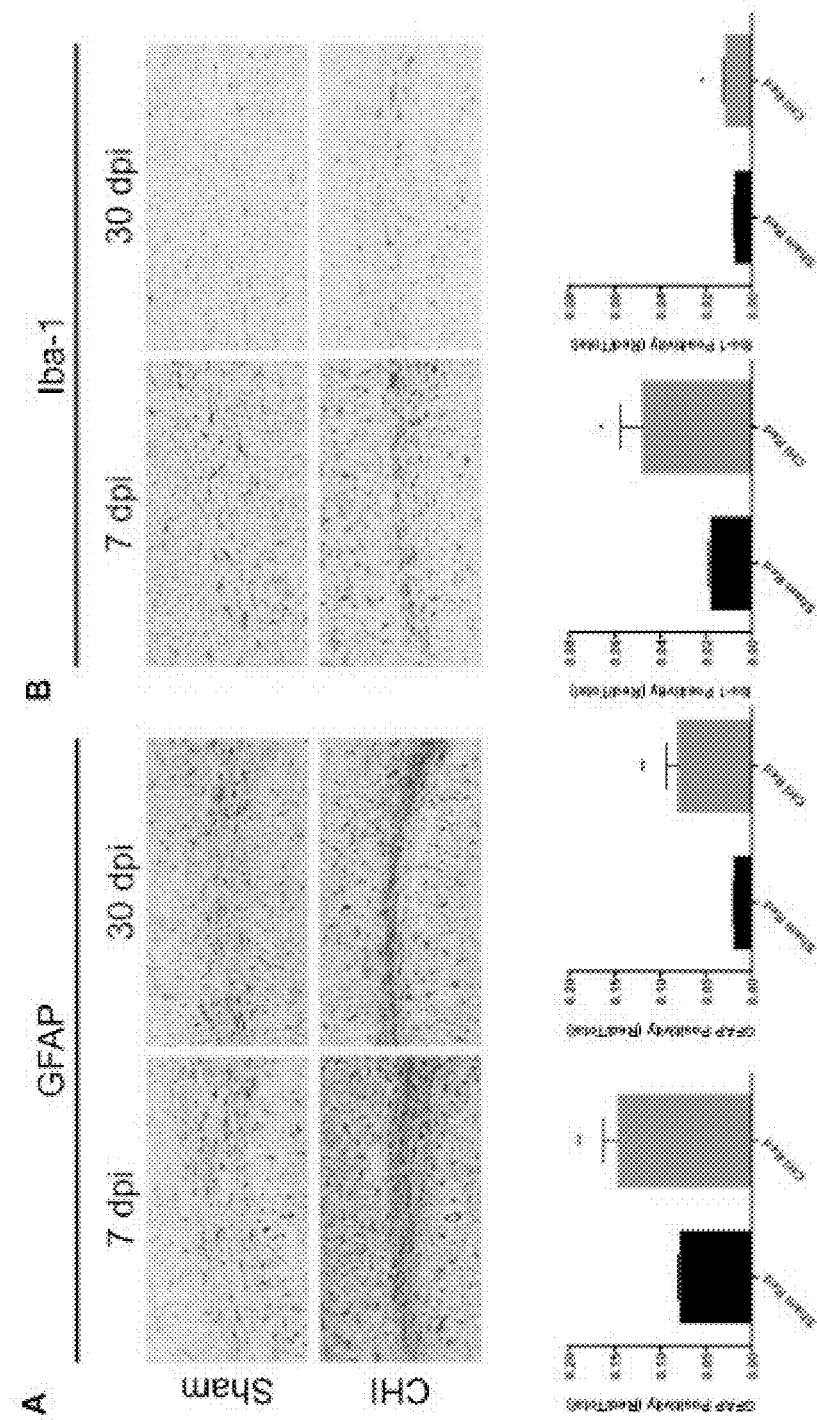
FIG. 24 panels A and B show representative images of external capsule brain sections from sham operated mice and from mice in a mouse closed head injury (CHI) model stained immunohistochemically for GFAP at 7 and 30 dpi and immunohistochemically for Iba-1 at 7 and 30 dpi, respectively, also shown below the representative stained sections are graphs showing the quantitative analysis of similar sections at 7 dpi on the left and at 30 dpi on the right for the same markers.

FIG. 24 panel A shows representative staining for GFAP in the external capsule of sham and CHI mice at 7 and 30 dpi and below the representative samples there is quatitiative analysis of the results from multiple mice. The representative sections show a dramatic increase in CFAP in the CHI mice that is sustained for at least 30 dpi. The quantitative results show significant increases in measured GFAP positivity at 7 and 30 dpi. The numbers and significance were: 7 dpi sham n=7 CHI n=8 and p=0.0019; 30 dpi sham n=7 and CHI n=11 p=0.0021. FIG. 24 panel B shows representative staining for Iba-1 in the external capsule of sham and CHI mice at 7 and 30 dpi and below the representative samples there is quatitiative analysis of the results from multiple mice. The representative sections show a dramatic increase in Iba-1 in the CHI mice that is very high after 7 dpi and still significantly elevated after 30 dpi. The quantitative data show that at 7 dpi there is a significant increase in the Iba-1 reactivity of the CHI mice. There is still a significant elevation at 30 dpi. The numbers and significance were as follows: 7 dpi sham n=6 and CHI n=7 *p=0.0181; at 30 dpi sham n=9 and CHI n=11 *p=0.0268.

Figure 25:
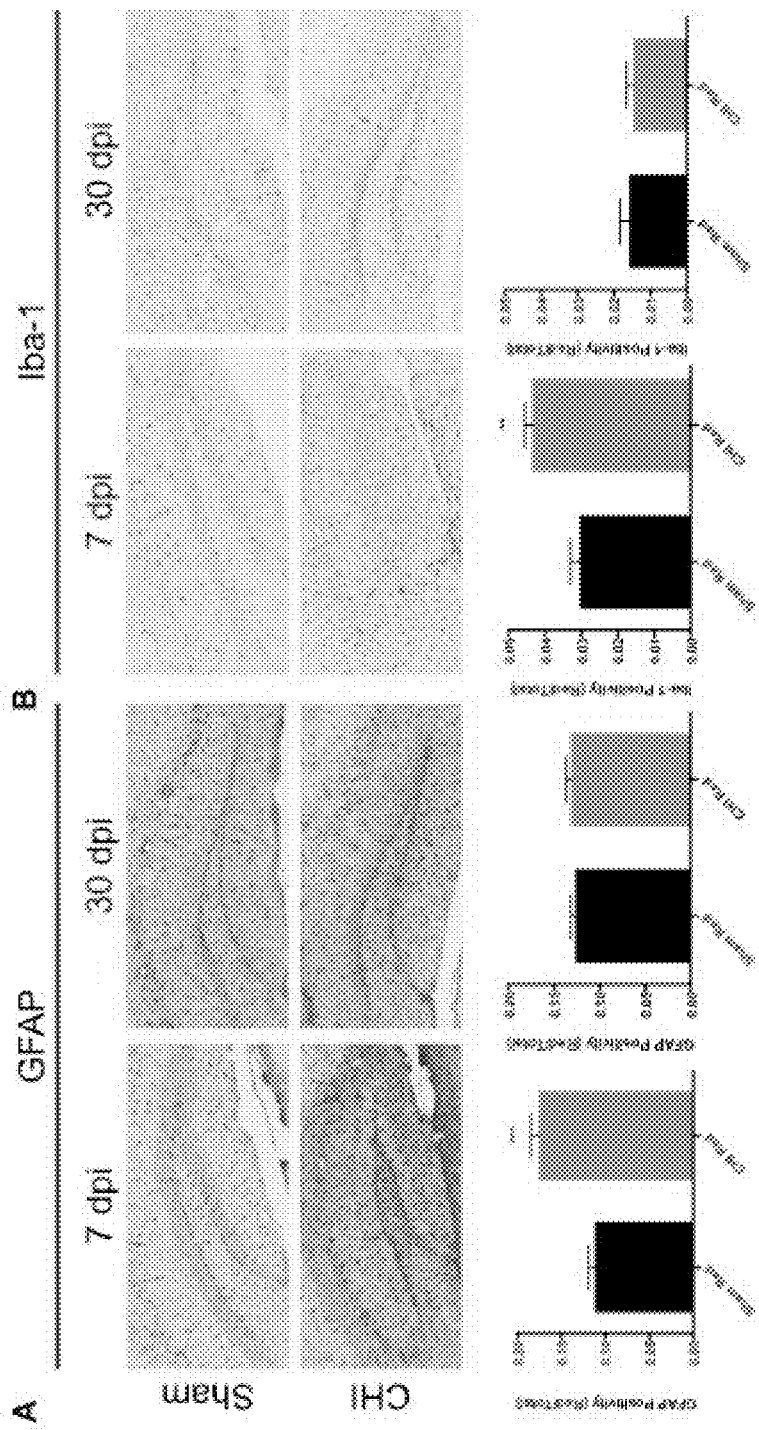
FIG. 25 panel A and B show representative images of dentate gyrus brain sections from sham operated mice and from mice in a mouse closed head injury (CHI) model stained immunohistochemically for GFAP at 7 and 30 dpi and immunohistochemically for Iba-1 at 7 and 30 dpi, respectively, also shown below the representative stained sections are graphs showing the quantitative analysis of similar sections after 7 days on the let and after 30 days on the right for the same markers.

FIG. 25 panel A shows representative staining for GFAP in the dentate gyrus of sham and CHI mice at 7 and 30 dpi and below the representative samples there is quatitiative analysis of the results from multiple mice. The representative sections show a significant increase in GFAP in the CHI mice that is resolved by 30 dpi. The quantitative results show significant increases in measured GFAP positivity at 7 dpi and a return to sham levels at 30 dpi. The numbers and significance were 7 dpi sham n=7 CHI n=7 and *p=0.0003; 30 dpi sham n=7 and CHI n=10. FIG. 25 panel B shows representative staining for Iba-1 in the external capsule of sham and CHI mice at 7 and 30 dpi and below the representative samples there is quatitiative analysis of the results from multiple mice. The representative sections show a significant increase in Iba-1 in the CHI mice at 7 dpi that is resolved after 30 dpi. The quantitative data show that at 7 dpi there is a significant increase in the Iba-1 reactivity of the CHI mice. The data also show that at 30 dpi the levels of GFAP are back to those found in sham mice. The numbers and significance were as follows: 7 dpi sham n=6 and CHI n=7 p=0.0054; at 30 dpi sham n=7 and CHI n=9. The dentate gyrus was the only area that showed resolution of inflammation, at least in terms of the level of reactive astrocytes and activated microglia, at 30 days post-injury. As this is the only region that undergoes neurogenesis, it is speculated that the active neurogenesis may play a role in brain repair, possibly by creating an environment rich in neurotrophic factors.

Figure 26:
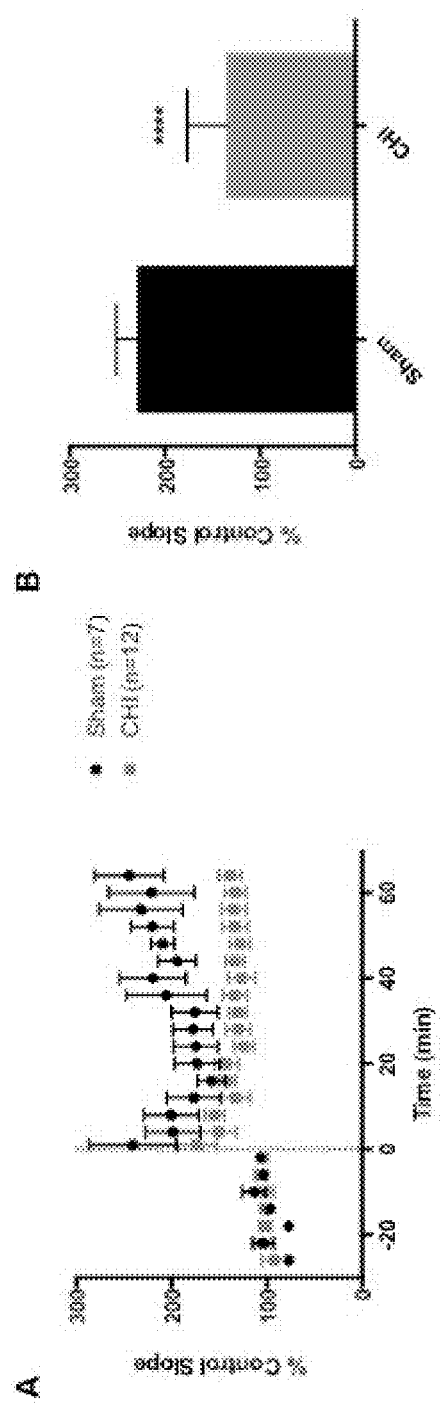
FIG. 26 panel A is a graph showing long-term potentiation (LTP) as the average of the initial slope of the fEPSP recording plotted over time normalized to the pre-High Frequency Stimulation (HFS) baseline from the CA1 stratum radiatum in response to stimulation of the Schaffer collaterals from CA3 of sham operated mice and from mice in a mouse closed head injury (CHI) model at 7 dpi, FIG. 26 panel B shows the averaged values at times 58-60 minutes in the same samples.

To examine the effect of neuroinflammation on cognitive functioning, long-term potentiation, the synaptic mechanism thought to underlie learning and memory, was examined at 7 dpi when abundant reactive astrocytes and microglia were present as shown in FIGS. 23-25. The results are presented in FIG. 26 panels A and B and were generated as described above in the rat FPI model. Hippocampal slices from CHI mice showed significantly less potentiation after high frequency stimulation (HFS) compared to slices from sham mice as shown in FIG. 26 panels A and B. The extent of long term potentiation (LTP) impairment was less than previously observed in our rat FPI model of TBI consistent with the severity of injury being much lower in the mouse CHI model. The numbers and significance were as follows: sham n=7 CHI n=12 and ****p<0.0001.

Figure 27:
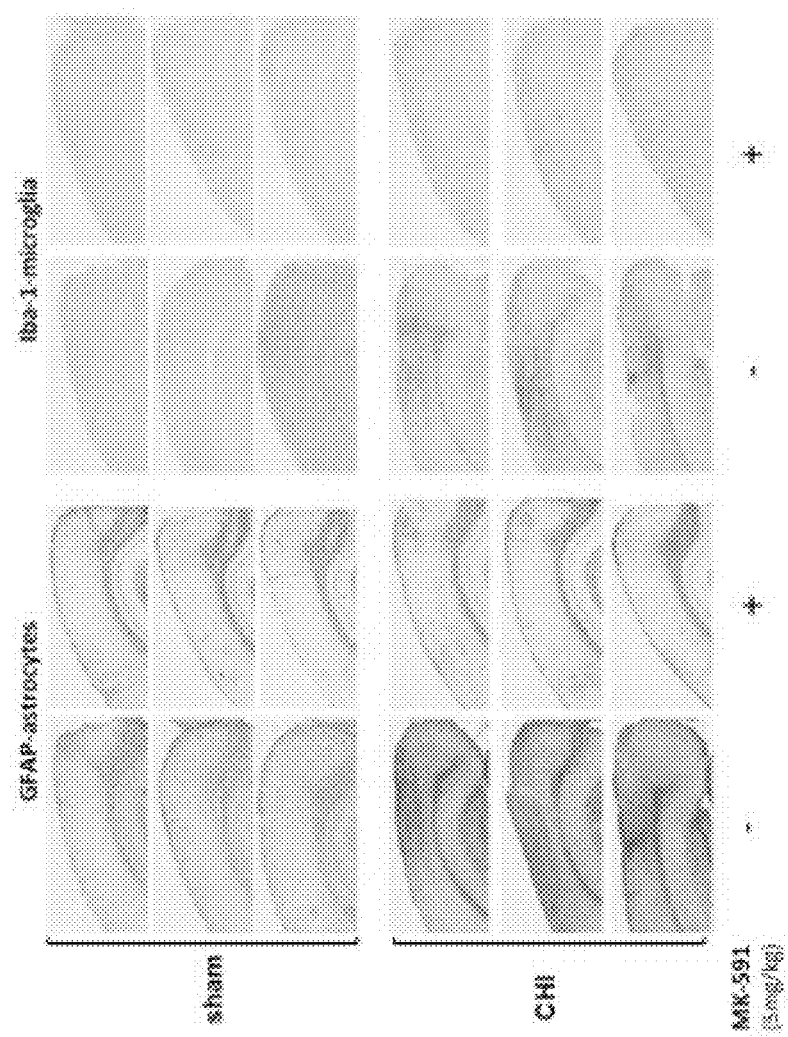
FIG. 27 shows representative images of GFAP and Iba-1 immunohistochemically stained cerebral cortex sections from sham operated mice and from mice in a mouse closed head injury model at 7 days post injury after the mice received vehicle (−) or MK591(+) 5 mg/kg via intraperitoneal injection once daily for 6 days prior to sacrifice and after injury.
Figure 28:
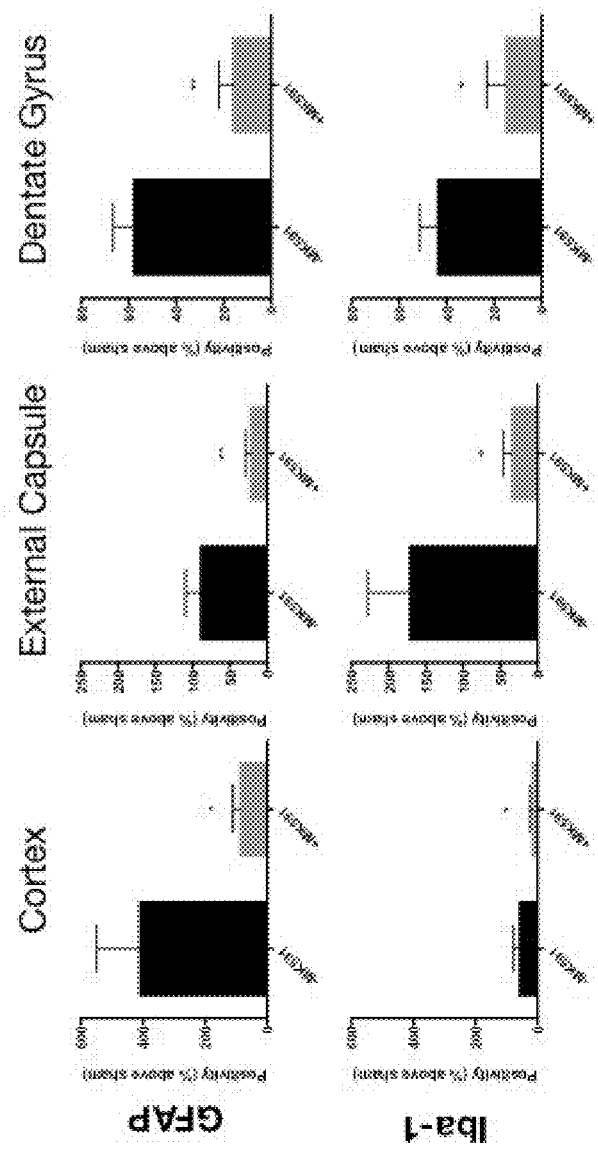
FIG. 28 shows quantitative analysis of GFAP and Iba-1 immunohistochemical staining of the cortex, external capsule, and dentate gyro of sham operated mice and of mice in a mouse closed head injury (CHI) model, at 7 dpi the mice received vehicle (−) or MK591(+) at 5 mg/kg via intraperitoneal injection once daily for 6 days prior to sacrifice.

As discussed above, FLAP inhibitors were efficacious in blocking edema, BBB disruption, cell loss, and cognitive impairment following a moderate FPI brain injury. To examine if FLAP inhibitors are capable of blocking prolonged neuroinflammation after mTBI, sham and CHI mice were administered either vehicle or MK-591 at 5 mg/kg, IP, 1× daily for 6 days after injury. At 7 dpi, mice were euthanized after cardiac perfusion and the fixed brains were removed, sectioned, and immunohistochemically stained for OFAP and Iba-1. FIG. 27 shows representative staining of the cerebral cortical region of 3 sham and 3 CHI mice that were treated with vehicle (−) or with MK-591 (+). There was markedly less staining of both GFAP and Iba-1 in CHI mice that had been injected with the FLAP inhibitor MK-591. The amount of GFAP and Iba-1 staining in the cerebral cortex, external capsule, and dentate gyrus of sham and CHI mice was quantified and the results are shown in FIG. 28. Administration of MK-591 for 6 days once daily following the CHI significantly blocked the increase of both OFAP and Iba-1 staining in all 3 regions of interest. These data indicate that FLAP inhibitors, not only block leukotriene-mediated inflammation shortly after TBI as observed in the rat FPI model of TBI, but that they are also efficacious in blocking neuroinflammation many days after a single CHI. The values in FIG. 28 are the mean+/−the SEM within each group and the data is reported as the percent positivity above sham for the groups +/−MK-591. The numbers and significance were as follows: −MK-591 sham n=7 CHI n=8; +MK-591 sham n=10 CHI n=10, the significance was *p<0.05 and **p<0.01.

Figure 29:
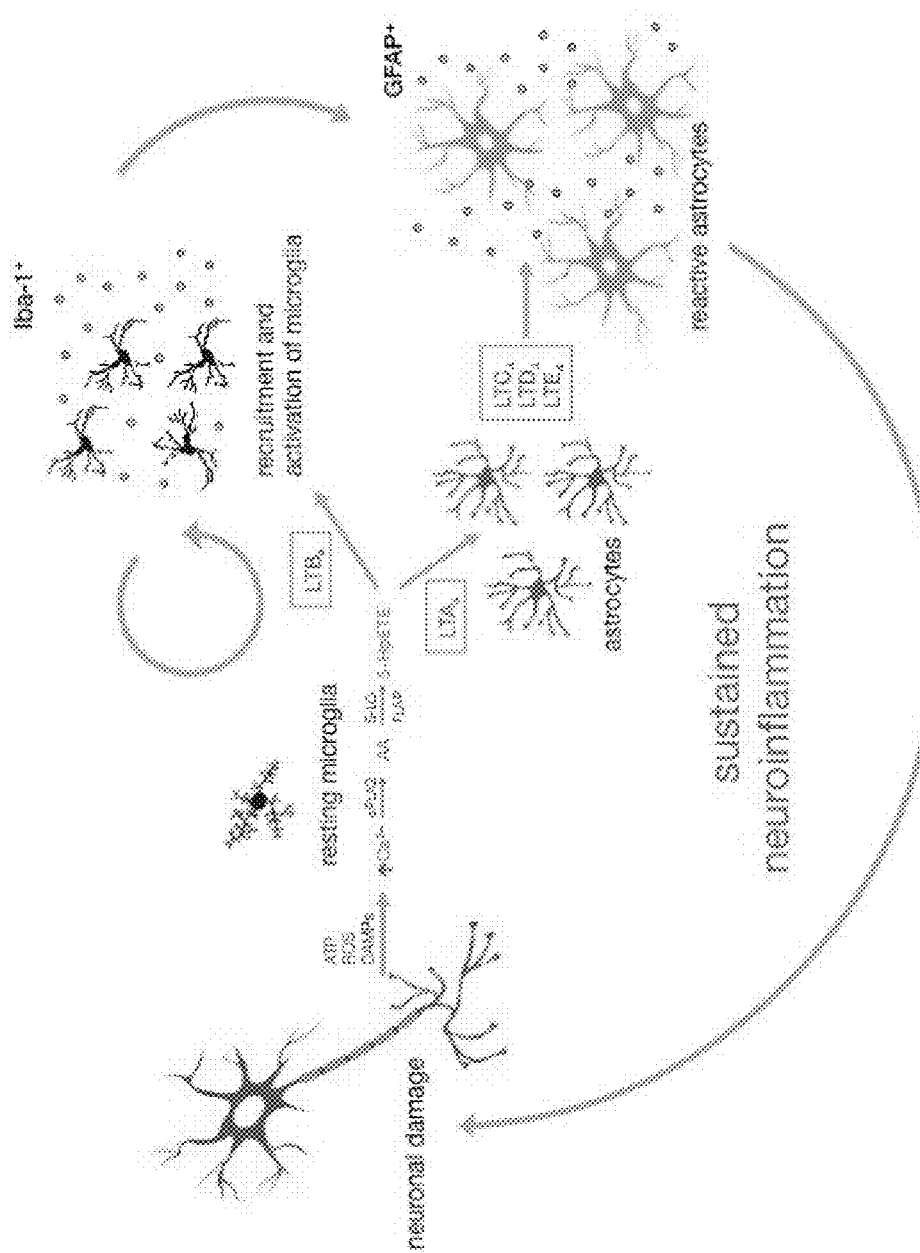
FIG. 29 shows a schematic of the sustained neuroinflammation pathway that is believed to exist following TBI from CHI, an experimental model of mTBI, based on the results presented in this invention.

FIG. 29 is a schematic representation of the role of leukotrienes in sustained neuroinflammation after a mTBI as shown in the CHI model of the present invention. Brain damage, for example diffuse axonal injury, results in the release of molecules from damaged axons including ATP which can bind to microglia and lead to calcium influx. Increased intracellular calcium activates cytoplasmic phospholipase 2 (cPLA$_2$) which cleaves membrane phospholipids generating free arachidonic acid (AA). The enzymes 5-LO and FLAP convert AA to a precursor LTA$_4$ that is converted to LTB$_4$, a potent chemotactic mediator that recruits additional immune cells to the area of injury. Alternatively or additionally the LTA$_4$ is converted to the cysteinyl-leukotrienes LTC$_4$, LTD$_4$, and LTE$_4$ known for their ability to stimulate cytokine and chernokine release and increase vascular permeability in more severe injury models that involve neutrophil infiltration. Leukotrienes can mount an inflammatory response to injury very quickly as the enzymes and substrates for producing these lipid mediators are already present in tissues thereby circumventing the need for transcriptional or translational events. If uninterrupted, the inflammatory response itself leads to further brain damage that acts in a positive feed-forward mechanism to promote more inflammation. The data of the present invention supports the theory that mTBI induces an innate neuroinflammatory response involving endogenous brain cells independent of peripheral immune cell infiltration. The ability of FLAP inhibitors to block this response is translatable to many human brain diseases that involve enhanced neuroinflammation or that might involve enhanced neuroinflammation.

The present invention is directed to preventing adverse effects of brain injury events including blood brain barrier (BBB) disruption and edema, early detrimental events that lead to additional cell death, axonal injury, and neurologic impairments. The present invention is also directed to reducing the longer term neuroinflammation believed to underlie many brain injury events. The present inventors have used two animal models of brain injury, specifically a fluid percussion injury TBI model in rats and a closed head injury (CHI) mTBI model in mice; however they believe that the results have implications for other brain injury events including stroke, multiple sclerosis, Alzheimer's disease, and post-traumatic stress disorder (PTSD). The inventors have discovered that blockade of leukotriene production by administration of FLAP inhibitors either before or shortly after a brain injury event significantly blocks edema, BBB disruption, cell death, cognitive and motor impairments, and longer term neuroinflammation that occur after a brain injury event. The most effective route of administration of the FLAP inhibitors is believed to be via an intranasal delivery method although other routes can be used including oral, intravenous, intraperitoneal, and via suppository. Administration of the FLAP inhibitors provides a dramatic reduction in the severity of a series of post-brain injury cell destruction events. Use of FLAP inhibitors prophylactically or shortly after a brain injury is expected to dramatically improve recovery of Hi brain function and to prevent many of the adverse consequences associated with brain injury events. The present inventors hypothesize that the results of the present invention support use of FLAP inhibitors in many brain injury events including TBI, stroke, multiple sclerosis, Alzheimer's disease, and post-traumatic stress disorder. The results suggest that the FLAP inhibitors can be used both prophylactically and after a brain injury event and still be effective. The effective dosage of any FLAP inhibitor will be determined in part by its IC50 and by its bioavailability as the ability of plasma proteins to bind many FLAP inhibitors can reduce their bioavailability. As discussed above under normal brain conditions there are no detectable leukotrienes in the brain nor is there evidence of neuroinflammation. Following many brain injury events, such as TBI, there is a dramatic rise in brain leukotrienes and evidence of longer term sustained neuroinflammation. Use of FLAP inhibitors in the central nervous system can ameliorate these brain injury associated events and prevent further CNS damage mediated by the rise in leukotrienes and neuroinflammation as shown in the present invention. The FLAP inhibitors are effective if provided prior to the brain injury event and if provided after the brain injury event. It is shown that providing the FLAP inhibitor 15 minutes prior to a brain injury event ran result in a significant reduction of the damage caused by the brain injury event. Longer time periods between administration of the FLAP inhibitor and the brain injury event are believed to be even more effective. Similarly, the FLAP inhibitor can be provided after a brain injury event and still provide protection against leukotriene increases and neuroinflammation.

The foregoing invention has been described in accordance with the relevant legal standards, thus the description is exemplary rather than limiting in nature. Variations and modifications to the disclosed embodiment may become apparent to those skilled in the art and do come within the scope of the invention. Accordingly, the scope of legal protection afforded this invention can only be determined by studying the following claims.

We claim:

1. A method of reducing neuroinflammation mediated damage in the central nervous system resulting from a closed head traumatic brain injury event in an animal comprising the steps of:
    identifying an animal having a closed head traumatic brain injury wherein said injury does not cause damage to the blood brain barrier or edema in the central nervous system of said animal;
    providing a 5-lipoxygenase activating protein (FLAP) inhibitor, wherein said FLAP inhibitor is able to cross the intact and undamaged blood brain barrier of said animal, and wherein said FLAP inhibitor is MK591;
    administering said FLAP inhibitor to said identified animal in an amount and at a time only after said closed head traumatic brain injury event wherein said amount and said time of delivery is sufficient for said FLAP inhibitor to cross said intact and undamaged blood brain barrier, enter brain tissue and to reduce a level of leukotrienes produced in said brain of said animal as a result of said closed head traumatic brain injury event and reducing neuroinflammation mediated damage in the central nervous system of said animal.

2. The method as recited in claim 1, wherein said animal is a human.

3. The method as recited in claim 1, wherein said FLAP inhibitor is administered by a route selected from the group consisting of an intravenous route, an intraperitoneal route, a suppository route, and an oral route.

4. The method as recited in claim 1, wherein said FLAP inhibitor is administered to said animal at least 15 minutes or more after said brain injury event.

5. The method as recited in claim 4, wherein said FLAP inhibitor is administered to said animal at least 1 time per day for at least 6 successive days following said brain injury event.

6. The method as recited in claim 1, wherein the leukotrienes reduced by said FLAP inhibitor comprise at least one of leukotriene $B_4$, leukotriene $C_4$, leukotriene $D_4$, leukotriene $E_4$, or a mixture thereof.

7. A method of reducing neuroinflammation mediated damage in the central nervous system resulting from a closed head traumatic brain injury event in an animal comprising the steps of:
    identifying an animal having a closed head traumatic brain injury wherein said injury does not cause damage to the blood brain barrier or edema in the central nervous system of said animal;
    providing a 5-lipoxygenase activating protein (FLAP) inhibitor, wherein said FLAP inhibitor is able to cross the intact and undamaged blood brain barrier of said animal and wherein said FLAP inhibitor is MK591;
    administering said FLAP inhibitor to said identified animal in an amount and at a time only after said closed head traumatic brain injury event wherein said amount and said time of delivery is sufficient for said FLAP inhibitor to cross said intact and undamaged blood brain barrier, enter brain tissue and to reduce said neuroinflammation mediated damage in the central nervous system as a result of said closed head traumatic brain injury event in said animal.

8. The method as recited in claim 7, wherein said animal is a human.

9. The method as recited in claim 7, wherein said FLAP inhibitor is administered by route selected from the group consisting of an intravenous route, an intraperitoneal route, a suppository route, and an oral route.

10. The method as recited in claim 7, wherein said FLAP inhibitor is administered to said animal at least 15 minutes after said brain injury event.

11. The method as recited in claim 10, wherein said FLAP inhibitor is administered to said animal at least 1 time per day for at least 6 successive days following said traumatic brain injury event.

12. The method as recited in claim 7, wherein said neuroinflammation mediated damage to the central nervous system reduced by said FLAP inhibitor comprises at least one of neuronal damage, neuronal death, astrocyte cell death and a cognitive deficit.

* * * * *